United States Patent
Sturmer et al.

(10) Patent No.: US 9,321,049 B2
(45) Date of Patent: Apr. 26, 2016

(54) CAPACITANCE DETECTION IN A DROPLET ACTUATOR

(71) Applicant: Advanced Liquid Logic, Inc., San Diego, CA (US)

(72) Inventors: Ryan A. Sturmer, Durham, NC (US); Michael G. Pollack, Durham, NC (US); Vamsee K. Pamula, Cary, NC (US); Vijay Srinivasan, Cary, NC (US); Philip Y. Paik, Chula Vista, CA (US)

(73) Assignee: ADVANCED LIQUID LOGIC, INC., San Diego, CA (US)

( * ) Notice: Subject to any disclaimer, the term of this patent is extended or adjusted under 35 U.S.C. 154(b) by 0 days.

(21) Appl. No.: 14/338,889

(22) Filed: Jul. 23, 2014

(65) Prior Publication Data

US 2014/0332380 A1    Nov. 13, 2014

Related U.S. Application Data

(63) Continuation of application No. 12/527,208, filed as application No. PCT/US2008/054134 on Feb. 15, 2008, now Pat. No. 8,872,527.

(60) Provisional application No. 60/980,520, filed on Oct. 17, 2007, provisional application No. 60/980,746, filed on Oct. 17, 2007, provisional application No. 60/889,966, filed on Feb. 15, 2007.

(51) Int. Cl.
*G01R 27/26* (2006.01)
*G01N 25/08* (2006.01)
(Continued)

(52) U.S. Cl.
CPC ....... *B01L 3/50273* (2013.01); *B01L 3/502784* (2013.01); *G01N 27/22* (2013.01);
(Continued)

(58) Field of Classification Search
CPC ............ G01R 27/2605; B01L 3/50273; B01L 3/502784; B01L 2300/0809; B01L 2300/0645; B01L 2400/0427; B01L 2300/0636; G01N 27/223; G01N 27/227; G01N 27/22; G01N 2203/00
USPC .................................. 324/658–690; 436/150
See application file for complete search history.

(56) References Cited

U.S. PATENT DOCUMENTS

| 4,636,785 A | 1/1987 | Le Pesant |
| 4,748,390 A | 5/1988 | Okushima et al. |

(Continued)

FOREIGN PATENT DOCUMENTS

| JP | 2006317364 A | 11/2006 |
| JP | 2006329899 A | 12/2006 |

(Continued)

OTHER PUBLICATIONS

PCT International Search Report and Written Opinion for PCT/US2008/054134 dated Jul. 30, 2008.
(Continued)

*Primary Examiner* — Benjamin M Baldridge
*Assistant Examiner* — Farhana Hoque
(74) *Attorney, Agent, or Firm* — William A. Barrett; Ward & Smith, P.A.

(57) ABSTRACT

A method, circuit and apparatus for detecting capacitance on a droplet actuator, inter alia, for determining the presence, partial presence or absence of a droplet at an electrode on a droplet actuator by: (a) providing a droplet actuator comprising: (i) a substrate comprising electrodes arranged on the substrate for conducting droplet operations on a surface of the substrate; (ii) a capacitance detection circuit for detecting capacitance at the droplet operations surface at one or more of the electrodes; (b) detecting capacitance at the droplet operations surface at one or more of the electrodes; and (c) determining from the capacitance the presence, partial presence or absence of a droplet at the droplet operations surface at the electrode.

3 Claims, 10 Drawing Sheets

(51) Int. Cl.
   *B01L 3/00* (2006.01)
   *G01N 27/22* (2006.01)

(52) U.S. Cl.
   CPC ........... *G01N 27/223* (2013.01); *G01N 27/227* (2013.01); *B01L 2300/0636* (2013.01); *B01L 2300/0645* (2013.01); *B01L 2300/0809* (2013.01); *B01L 2400/0427* (2013.01); *G01N 2203/00* (2013.01)

(56) References Cited

U.S. PATENT DOCUMENTS

| | | | |
|---|---|---|---|
| 4,936,828 A | 6/1990 | Chiang | |
| 5,181,016 A | 1/1993 | Lee et al. | |
| 5,486,337 A | 1/1996 | Ohkawa et al. | |
| 6,063,339 A | 5/2000 | Tisone et al. | |
| 6,078,384 A | 6/2000 | Dammann et al. | |
| 6,130,098 A | 10/2000 | Handique et al. | |
| 6,294,063 B1 | 9/2001 | Becker et al. | |
| 6,379,929 B1 | 4/2002 | Burns et al. | |
| 6,565,727 B1 | 5/2003 | Shenderov | |
| 6,773,566 B2 | 8/2004 | Shenderov | |
| 6,790,011 B1 | 9/2004 | Le Pesant et al. | |
| 6,911,132 B2 * | 6/2005 | Pamula ............ B01F 11/0071 204/600 | |
| 6,924,792 B1 | 8/2005 | Jessop | |
| 6,977,033 B2 | 12/2005 | Becker et al. | |
| 6,989,234 B2 | 1/2006 | Kolar et al. | |
| 7,052,244 B2 | 5/2006 | Fouillet et al. | |
| 7,148,683 B2 | 12/2006 | Xiang et al. | |
| 7,163,612 B2 | 1/2007 | Sterling et al. | |
| 7,211,223 B2 | 5/2007 | Fouillet et al. | |
| 7,255,780 B2 | 8/2007 | Shenderov | |
| 7,328,979 B2 | 2/2008 | Decre et al. | |
| 7,329,545 B2 | 2/2008 | Pamula et al. | |
| 7,439,014 B2 | 10/2008 | Pamula et al. | |
| 7,439,072 B2 | 10/2008 | Shvets et al. | |
| 7,458,661 B2 | 12/2008 | Kim et al. | |
| 7,531,072 B2 | 5/2009 | Roux et al. | |
| 7,547,380 B2 | 6/2009 | Velev | |
| 7,569,129 B2 | 8/2009 | Pamula et al. | |
| 7,641,779 B2 | 1/2010 | Becker et al. | |
| 7,727,466 B2 | 6/2010 | Meathrel et al. | |
| 7,727,723 B2 | 6/2010 | Pollack et al. | |
| 7,759,132 B2 | 7/2010 | Pollack et al. | |
| 7,763,471 B2 | 7/2010 | Pamula et al. | |
| 7,815,871 B2 | 10/2010 | Pamula et al. | |
| 7,816,121 B2 | 10/2010 | Pollack et al. | |
| 7,822,510 B2 | 10/2010 | Paik et al. | |
| 7,851,184 B2 | 12/2010 | Pollack et al. | |
| 7,875,160 B2 | 1/2011 | Jary | |
| 7,901,947 B2 | 3/2011 | Pollack et al. | |
| 7,919,330 B2 | 4/2011 | De Guzman et al. | |
| 7,922,886 B2 | 4/2011 | Fouillet et al. | |
| 7,939,021 B2 | 5/2011 | Smith et al. | |
| 7,943,030 B2 | 5/2011 | Shenderov | |
| 7,989,056 B2 | 8/2011 | Plissonnier et al. | |
| 7,998,436 B2 | 8/2011 | Pollack | |
| 8,007,739 B2 | 8/2011 | Pollack et al. | |
| 8,041,463 B2 | 10/2011 | Pollack et al. | |
| 8,048,628 B2 | 11/2011 | Pollack et al. | |
| 8,075,754 B2 | 12/2011 | Sauter-Starace et al. | |
| 8,093,062 B2 | 1/2012 | Winger et al. | |
| 8,137,917 B2 | 3/2012 | Pollack et al. | |
| 8,147,668 B2 | 4/2012 | Pollack et al. | |
| 8,202,686 B2 | 6/2012 | Pamula et al. | |
| 8,208,146 B2 | 6/2012 | Srinivasan et al. | |
| 8,221,605 B2 | 7/2012 | Pollack et al. | |
| 8,236,156 B2 | 8/2012 | Sarrut et al. | |
| 8,268,246 B2 | 9/2012 | Srinivasan et al. | |
| 8,287,711 B2 | 10/2012 | Pollack et al. | |
| 8,304,253 B2 | 11/2012 | Yi et al. | |
| 8,313,698 B2 | 11/2012 | Pollack et al. | |
| 8,317,990 B2 | 11/2012 | Pamula et al. | |
| 8,342,207 B2 | 1/2013 | Raccurt et al. | |
| 8,349,276 B2 | 1/2013 | Pamula et al. | |
| 8,388,909 B2 | 3/2013 | Pollack et al. | |
| 8,389,297 B2 | 3/2013 | Pamula et al. | |
| 8,394,249 B2 | 3/2013 | Pollack et al. | |
| 8,426,213 B2 | 4/2013 | Eckhardt et al. | |
| 8,440,392 B2 | 5/2013 | Pamula et al. | |
| 8,444,836 B2 | 5/2013 | Fouillet et al. | |
| 8,872,527 B2 | 10/2014 | Sturmer et al. | |
| 2002/0005354 A1 | 1/2002 | Spence et al. | |
| 2002/0036139 A1 | 3/2002 | Becker et al. | |
| 2002/0043463 A1 | 4/2002 | Shenderov | |
| 2002/0058332 A1 | 5/2002 | Quake et al. | |
| 2002/0143437 A1 | 10/2002 | Handique et al. | |
| 2003/0071639 A1 | 4/2003 | Haag et al. | |
| 2003/0164295 A1 | 9/2003 | Sterling | |
| 2003/0183525 A1 | 10/2003 | Elrod et al. | |
| 2003/0184316 A1 * | 10/2003 | Yamagishi et al. | 324/663 |
| 2003/0205632 A1 | 11/2003 | Kim et al. | |
| 2004/0027405 A1 | 2/2004 | Stoessel et al. | |
| 2004/0031688 A1 | 2/2004 | Shenderov | |
| 2004/0055891 A1 | 3/2004 | Pamula et al. | |
| 2004/0058450 A1 | 3/2004 | Pamula et al. | |
| 2004/0231987 A1 | 11/2004 | Sterling et al. | |
| 2006/0021875 A1 | 2/2006 | Griffith et al. | |
| 2006/0054503 A1 | 3/2006 | Pamula et al. | |
| 2006/0114296 A1 | 6/2006 | Gascoyne et al. | |
| 2006/0164490 A1 | 7/2006 | Kim et al. | |
| 2006/0194331 A1 | 8/2006 | Pamula et al. | |
| 2006/0231398 A1 | 10/2006 | Sarrut et al. | |
| 2006/0254933 A1 | 11/2006 | Adachi et al. | |
| 2006/0286549 A1 | 12/2006 | Sohn et al. | |
| 2007/0015289 A1 | 1/2007 | Kao et al. | |
| 2007/0019041 A1 | 1/2007 | Mataki | |
| 2007/0023292 A1 | 2/2007 | Kim et al. | |
| 2007/0037294 A1 | 2/2007 | Pamula et al. | |
| 2007/0045117 A1 | 3/2007 | Pamula et al. | |
| 2007/0064990 A1 | 3/2007 | Roth | |
| 2007/0086927 A1 | 4/2007 | Natarajan et al. | |
| 2007/0207513 A1 | 9/2007 | Sorensen et al. | |
| 2007/0217956 A1 | 9/2007 | Pamula et al. | |
| 2007/0241068 A1 | 10/2007 | Pamula et al. | |
| 2007/0242105 A1 | 10/2007 | Srinivasan et al. | |
| 2007/0242111 A1 | 10/2007 | Pamula et al. | |
| 2007/0243634 A1 | 10/2007 | Pamula et al. | |
| 2007/0267294 A1 | 11/2007 | Shenderov | |
| 2007/0275415 A1 | 11/2007 | Srinivasan et al. | |
| 2008/0006535 A1 | 1/2008 | Paik et al. | |
| 2008/0038810 A1 | 2/2008 | Pollack et al. | |
| 2008/0044893 A1 | 2/2008 | Pollack et al. | |
| 2008/0044914 A1 | 2/2008 | Pamula et al. | |
| 2008/0050834 A1 | 2/2008 | Pamula et al. | |
| 2008/0053205 A1 | 3/2008 | Pollack et al. | |
| 2008/0105549 A1 | 5/2008 | Pamela et al. | |
| 2008/0124252 A1 | 5/2008 | Marchand et al. | |
| 2008/0142376 A1 | 6/2008 | Fouillet et al. | |
| 2008/0151240 A1 | 6/2008 | Roth | |
| 2008/0210558 A1 | 9/2008 | Sauter-Starace et al. | |
| 2008/0231291 A1 | 9/2008 | Ramsey et al. | |
| 2008/0247920 A1 | 10/2008 | Pollack et al. | |
| 2008/0264797 A1 | 10/2008 | Pamula et al. | |
| 2008/0274513 A1 | 11/2008 | Shenderov et al. | |
| 2008/0281471 A1 | 11/2008 | Smith et al. | |
| 2008/0283414 A1 | 11/2008 | Monroe et al. | |
| 2008/0302431 A1 | 12/2008 | Marchand et al. | |
| 2008/0305481 A1 | 12/2008 | Whitman et al. | |
| 2009/0014394 A1 | 1/2009 | Yi et al. | |
| 2009/0042319 A1 | 2/2009 | De Guzman et al. | |
| 2009/0127123 A1 | 5/2009 | Raccurt et al. | |
| 2009/0134027 A1 | 5/2009 | Jary | |
| 2009/0142564 A1 | 6/2009 | Plissonnier et al. | |
| 2009/0155902 A1 | 6/2009 | Pollack et al. | |
| 2009/0192044 A1 | 7/2009 | Fouillet | |
| 2009/0260988 A1 | 10/2009 | Pamula et al. | |
| 2009/0263834 A1 | 10/2009 | Sista et al. | |
| 2009/0280251 A1 | 11/2009 | De Guzman et al. | |
| 2009/0280475 A1 | 11/2009 | Pollack et al. | |
| 2009/0280476 A1 | 11/2009 | Srinivasan et al. | |
| 2009/0288710 A1 | 11/2009 | Viovy et al. | |
| 2009/0291433 A1 | 11/2009 | Pollack et al. | |

(56) References Cited

U.S. PATENT DOCUMENTS

| | | |
|---|---|---|
| 2009/0304944 A1 | 12/2009 | Sudarsan et al. |
| 2009/0321262 A1 | 12/2009 | Adachi et al. |
| 2010/0025242 A1 | 2/2010 | Pamula et al. |
| 2010/0025250 A1 | 2/2010 | Pamula et al. |
| 2010/0028920 A1 | 2/2010 | Eckhardt |
| 2010/0032293 A1 | 2/2010 | Pollack et al. |
| 2010/0041086 A1 | 2/2010 | Pamula et al. |
| 2010/0048410 A1 | 2/2010 | Shenderov et al. |
| 2010/0062508 A1 | 3/2010 | Pamula et al. |
| 2010/0068764 A1 | 3/2010 | Sista et al. |
| 2010/0087012 A1 | 4/2010 | Shenderov et al. |
| 2010/0096266 A1 | 4/2010 | Kim et al. |
| 2010/0116640 A1 | 5/2010 | Pamula et al. |
| 2010/0118307 A1 | 5/2010 | Srinivasan et al. |
| 2010/0120130 A1 | 5/2010 | Srinivasan et al. |
| 2010/0126860 A1 | 5/2010 | Srinivasan et al. |
| 2010/0130369 A1 | 5/2010 | Shenderov et al. |
| 2010/0140093 A1 | 6/2010 | Pamula et al. |
| 2010/0143963 A1 | 6/2010 | Pollack |
| 2010/0151439 A1 | 6/2010 | Pamula et al. |
| 2010/0181195 A1 | 7/2010 | Garcia Tello |
| 2010/0194408 A1 | 8/2010 | Sturmer et al. |
| 2010/0236927 A1 | 9/2010 | Pope et al. |
| 2010/0236928 A1 | 9/2010 | Srinivasan et al. |
| 2010/0236929 A1 | 9/2010 | Pollack et al. |
| 2010/0258441 A1 | 10/2010 | Sista et al. |
| 2010/0270156 A1 | 10/2010 | Srinivasan et al. |
| 2010/0279374 A1 | 11/2010 | Sista et al. |
| 2010/0282608 A1 | 11/2010 | Srinivasan et al. |
| 2010/0282609 A1 | 11/2010 | Pollack et al. |
| 2010/0307917 A1 | 12/2010 | Srinivasan et al. |
| 2010/0320088 A1 | 12/2010 | Fouillet et al. |
| 2010/0323405 A1 | 12/2010 | Pollack et al. |
| 2011/0086377 A1 | 4/2011 | Thwar et al. |
| 2011/0100823 A1 | 5/2011 | Pollack et al. |
| 2011/0104725 A1 | 5/2011 | Pamula et al. |
| 2011/0114490 A1 | 5/2011 | Pamula et al. |
| 2011/0118132 A1 | 5/2011 | Winger et al. |
| 2011/0180571 A1 | 7/2011 | Srinivasan et al. |
| 2011/0186433 A1 | 8/2011 | Pollack et al. |
| 2011/0203930 A1 | 8/2011 | Pamula et al. |
| 2011/0209998 A1 | 9/2011 | Shenderov |
| 2011/0303542 A1 | 12/2011 | Srinivasan et al. |
| 2012/0018306 A1 | 1/2012 | Srinivasan et al. |
| 2012/0132528 A1 | 5/2012 | Shenderov et al. |
| 2012/0165238 A1 | 6/2012 | Pamula et al. |
| 2013/0018611 A1 | 1/2013 | Sturmer |
| 2013/0168250 A1 | 7/2013 | Fogleman et al. |
| 2013/0293246 A1 | 11/2013 | Pollack et al. |
| 2014/0190830 A1 | 7/2014 | Sturmer et al. |

FOREIGN PATENT DOCUMENTS

| | | |
|---|---|---|
| JP | 2006329904 A | 12/2006 |
| WO | 0069565 A1 | 11/2000 |
| WO | 0073655 A1 | 12/2000 |
| WO | 2004029585 A1 | 4/2004 |
| WO | 2004030820 | 4/2004 |
| WO | 2005047696 A1 | 5/2005 |
| WO | 2006013303 A1 | 2/2006 |
| WO | 2006070162 A1 | 7/2006 |
| WO | 2006081558 | 8/2006 |
| WO | 2006124458 A2 | 11/2006 |
| WO | 2006127451 A2 | 11/2006 |
| WO | 2006134307 A1 | 12/2006 |
| WO | 2006138543 | 12/2006 |
| WO | 2007003720 A1 | 1/2007 |
| WO | 2007012638 A1 | 2/2007 |
| WO | 2007033990 A1 | 3/2007 |
| WO | 2007048111 | 4/2007 |
| WO | 2007120240 A2 | 10/2007 |
| WO | 2007120241 A2 | 10/2007 |
| WO | 2007123908 A2 | 11/2007 |
| WO | 2008051310 A2 | 5/2008 |
| WO | 2008055256 A3 | 5/2008 |
| WO | 2008068229 A1 | 6/2008 |
| WO | 2008091848 A2 | 7/2008 |
| WO | WO2008091848 | 7/2008 |
| WO | 2008098236 A2 | 8/2008 |
| WO | 2008101194 A2 | 8/2008 |
| WO | 2008106678 A1 | 9/2008 |
| WO | 2008109664 A1 | 9/2008 |
| WO | 2008112856 A1 | 9/2008 |
| WO | 2008116209 A1 | 9/2008 |
| WO | 2008116221 A1 | 9/2008 |
| WO | 2008118831 A2 | 10/2008 |
| WO | 2008124846 A2 | 10/2008 |
| WO | 2008131420 A2 | 10/2008 |
| WO | 2008134153 A1 | 11/2008 |
| WO | 2009002920 A1 | 12/2008 |
| WO | 2009003184 A1 | 12/2008 |
| WO | 2009011952 A1 | 1/2009 |
| WO | 2009021173 A1 | 2/2009 |
| WO | 2009021233 A2 | 2/2009 |
| WO | 2009026339 A2 | 2/2009 |
| WO | 2009029561 A2 | 3/2009 |
| WO | 2009032863 A2 | 3/2009 |
| WO | 2009052095 A1 | 4/2009 |
| WO | 2009052123 A2 | 4/2009 |
| WO | 2009052321 A2 | 4/2009 |
| WO | 2009052345 A2 | 4/2009 |
| WO | 2009052348 A2 | 4/2009 |
| WO | 2009076414 | 6/2009 |
| WO | 2009086403 A2 | 7/2009 |

OTHER PUBLICATIONS

Chakrabarty, "Automated Design of Microfluidics-Based Biochips: connecting Biochemistry of Electronics CAD", IEEE International Conference on Computer Design, San Jose, CA, Oct. 1-4, 2006, 93-100.

Chakrabarty et al., "Design Automation Challenges for Microfluidics-Based Biochips", DTIP of MEMS & MOEMS, Montreux, Switzerland, Jun. 1-3, 2005.

Chakrabarty et al., "Design Automation for Microfluidics-Based Biochips", ACM Journal on Engineering Technologies in Computing Systems , 1(3), Oct. 2005, 186-223.

Chakrabarty, "Design, Testing, and Applications of Digital Microfluidics-Based Biochips", Proceedings of the 18th International Conf. on VLSI held jointly with 4th International Conf. on Embedded Systems Design (VLSID'05), IEEE, Jan. 3-7, 2005.

Chen et al., "Development of Mesoscale Actuator Device with Micro Interlocking Mechanism", J. Intelligent Material Systems and Structures, vol. 9, No. 4, Jun. 1998, pp. 449-457.

Chen et al., "Mesoscale Actuator Device with Micro Interlocking Mechanism", Proc. IEEE Micro Electro Mechanical Systems Workshop, Heidelberg, Germany, Jan. 1998, pp. 384-389.

Chen et al., "Mesoscale Actuator Device: Micro Interlocking Mechanism to Transfer Macro Load", Sensors and Actuators, vol. 73, Issues 1-2, Mar. 1999, pp. 30-36.

Dewey, "Towards a Visual Modeling Approach to Designing Microelectromechanical System Transducers", Journal of Micromechanics and Microengineering, vol. 9, Dec. 1999, 332-340.

Dewey et al., "Visual modeling and design of microelectromechanical system tansducers", Microelectronics Journal, vol. 32, Apr. 2001, 373-381.

Fair et al., "A Micro-Watt Metal-Insulator-Solution-Transport (MIST) Device for Scalable Digital Bio-Microfluidic Systems", IEEE IEDM Technical Digest, 2001, 16.4.1-4.

Fair et al., "Advances in droplet-based bio lab-on-a-chip", BioChips 2003, Boston, 2003.

Fair et al., "Bead-Based and Solution-Based Assays Performed on a Digital Microfluidic Platform", Biomedical Engineering Society (BMES) Fall Meeting, Baltimore, MD, Oct. 1, 2005.

Fair, "Biomedical Applications of Electrowetting Systems", 5th International Electrowetting Workshop, Rochester, NY, May 31, 2006.

Fair et al., "Chemical and Biological Applications of Digital-Microfluidic Devices", IEEE Design & Test of Computers, vol. 24(1), Jan.-Feb. 2007, 10-24.

(56) References Cited

OTHER PUBLICATIONS

Fair et al., "Chemical and biological pathogen detection in a digital microfluidic platform", DARPA Workshop on Microfluidic Analyzers for DoD and National Security Applications, Keystone, CO, 2006.
Fair, "Digital microfluidics: is a true lab-on-a-chip possible?", Microfluid Nanofluid, vol. 3, Mar. 8, 2007, 245-281.
Fair, "Droplet-based microfluidic Genome sequencing", NHGRI PI's meeting, Boston, 2005.
Fair et al., "Electrowetting-based On-Chip Sample Processing for Integrated Microfluidics", IEEE Inter. Electron Devices Meeting (IEDM), 2003, 32.5.1-32.5.4.
Fair et al., "Integrated chemical/biochemical sample collection, pre-concentration, and analysis on a digital microfluidic lab-on-a-chip platform", Lab-on-a-Chip: Platforms, Devices, and Applications, Conf. 5591, SPIE Optics East, Philadelphia, Oct. 25-28, 2004.
Fouillet et al., "Design and Validation of a Complex Generic Fluidic Microprocessor Based on EWOD Droplet for Biological Applications", 9th International Conference on Miniaturized Systems for Chem and Life Sciences, Boston, MA, Oct. 9-13, 2005, 58-60.
Jun et al., "Valveless Pumping using Traversing Vapor Bubbles in Microchannels", J. Applied Physics, vol. 83, No. 11, Jun. 1998, pp. 5658-5664.
Kim et al., "MEMS Devices Based on the Use of Surface Tension", Proc. Int. Semiconductor Device Research Symposium (ISDRS'99), Charlottesville, VA, Dec. 1999, pp. 481-484.
Kim, "Microelectromechanical Systems (MEMS) at the UCLA Micromanufacturing Lab", Dig. Papers, Int. Microprocesses and Nanotechnology Conf. (MNC'98), Kyungju, Korea, Jul. 1998, pp. 54-55.
Kim et al., "Micromachines Driven by Surface Tension", AIAA 99-3800, 30th AIAA Fluid Dynamics Conference, Norfolk, VA, (Invited lecture), Jun. 1999, pp. 1-6.
Lee et al., "Microactuation by Continuous Electrowetting Phenomenon and Silicon Deep Rie Process", Proc. MEMS (DSC—vol. 66) ASME Int. Mechanical Engineering Congress and Exposition, Anaheim, CA, Nov. 1998, 475-480.
Lee et al., "Liquid Micromotor Driven by Continuous Electrowetting", Proc. IEEE Micro Electro Mechanical Systems Workshop, Heidelberg, Germany, Jan. 1998, pp. 538-543.
Lee et al., "Theory and Modeling of Continuous Electrowetting Microactuation", Proc. MEMS (MEMS—vol. 1), ASME Int. Mechanical Engineering Congress and Exposition, Nashville, TN, Nov. 1999, pp. 397-403.
Paik et al., "Adaptive Cooling of Integrated Circuits Using Digital Microfluidics", accepted for publication in IEEE Transactions on VLSI Systems, 2007, and Artech House, Norwood, MA, 2007.
Paik, "Adaptive Hot-Spot Cooling of Integrated Circuits Using Digital Microfluidics", Dissertation, Dept. of Electrical and Computer Engineering, Duke University, Apr. 25, 2006, 1-188.
Paik et al., "Adaptive hot-spot cooling of integrated circuits using digital microfluidics", Proceedings ASME International Mechanical Engineering Congress and Exposition, Orlando, Florida, USA. IMECE2005-81081, Nov. 5-11, 2005, 1-6.
Paik et al., "Coplanar Digital Microfluidics Using Standard Printed Circuit Board Processes", 9th International Conference on Miniaturized Systems for Chemistry and Life Sciences (MicroTAS), Boston, MA; Poster, 2005.
Paik et al., "Coplanar Digital Microfluidics Using Standard Printed Circuit Board Processes", 9th Int'l Conf. on Miniaturized Systems for Chemistry and Life Sciences, Boston, MA, Oct. 9-13, 2005, 566-68.
Paik et al., "Droplet-Based Hot Spot Cooling Using Topless Digital Microfluidics on a Printed Circuit Board", Int'l Workshops on Thermal Investigations of ICs and Systems (THERMINIC), 2005, 278-83.
Paik et al., "Electrowetting-based droplet mixers for microfluidic systems", Lab on a Chip (LOC), vol. 3. (more mixing videos available, along with the article, at LOC's website), 2003, 28-33.
Paik et al., "Programmable Flow-Through Real Time PCR Using Digital Microfluidics", 11th International Conference on Miniaturized Systems for Chemistry and Life Sciences, Paris, France, Oct. 7-11, 2007, 1559-1561.
Paik et al., "Programmable flow-through real-time PCR using digital microfluidics", Proc. Micro Total Analysis Systems (µTAS), Handout, 2007.
Paik et al., "Programmable flow-through real-time PCR using digital microfluidics", Proc. Micro Total Analysis Systems (µTAS), Poster, 2007.
Paik et al., "Rapid Droplet Mixers for Digital Microfluidic Systems", Masters Thesis, Duke Graduate School., 2002, 1-82.
Paik et al., "Rapid droplet mixers for digital microfluidic systems", Lab on a Chip, vol. 3. (More mixing videos available, along with the article, at LOC's website.), 2003, 253-259.
Paik et al., "Thermal effects on Droplet Transport in Digital Microfluids with Application to Chip Cooling Processing for Integrated Microfluidics", International Conference on Thermal, Mechanics, and Thermomechanical Phenomena in Electronic Systems (ITherm), 2004, 649-654.
Pamula, "A digital microfluidic platform for multiplexed explosive detection", Chapter 18, Electronics Noses and Sensors for the Detection of Explosives, Eds., J.W. Gardner and J. Yinon, Kluwer Academic Publishers, 2004.
Pamula et al., "A droplet-based lab-on-a-chip for colorimetric detection of nitroaromatic explosives", Proceedings of Micro Electro Mechanical Systems, 2005, 722-725.
Pamula et al., "Cooling of integrated circuits using droplet-based microfluidics", Proc. ACM Great Lakes Symposium on VLSI, Apr. 2003, 84-87.
Pamula et al., "Digital microfluidic lab-on-a-chip for protein crystallization", 5th Protein Structure Initiative "Bottlenecks" Workshop, NIH, Bethesda, MD, Apr. 13-14, 2006, I-16.
Pamula et al., "Digital Microfluidics Platform for Lab-on-a-chip applications", Duke University Annual Post Doctoral Research Day, 2002.
Pamula et al., "Microfluidic electrowetting-based droplet mixing", IEEE, 2002, 8-10.
Pamula et al. (Co-Chair, "Digital Microfluidics for Lab-on-a-Chip Applications", "Emerging CAD Challenges for Biochip Design" Workshop, Conference on Design, Automation, and Test in Europe (DATE), Munich, Germany, Advance Programme, 2006, pp. 85-87.
Pollack, et al., "Electrowetting-Based Actuation of Droplets for Integrated Microfluidics", Lab on a Chip (LOC), vol. 2, 2002, 96-101.
Pollack et al., "Electrowetting-based actuation of liquid droplets for microfluidic applications", Appl. Phys. Letters, vol. 77, No. 11, Sep. 11, 2000, 1725-1726.
Pollack, "Electrowetting-based Microactuation of Droplets for Digital Microfluidics", PhD Thesis, Department of Electrical and Computer Engineering, Duke University, 2001.
Pollack et al., "Electrowetting-Based Microfluidics for High-Throughput Screening", smallTalk 2001 Conference Program Abstract, San Diego, Aug. 27-31, 2001, 149.
Pollack et al., "Investigation of electrowetting-based microfluidics for real-time PCR applications", Proc. 7th Int'l Conference on Micro Total Analysis Systems (mTAS), Squaw Valley, CA, Oct. 5-9, 2003, 619-622.
Ren et al., "Automated electrowetting-based droplet dispensing with good reproducibility", Proc. Micro Total Analysis Systems (mTAS), 7th Int. Conf.on Miniaturized Chem and Biochem Analysis Systems, Squaw Valley, CA, Oct. 5-9, 2003, 993-996.
Ren et al., "Automated on-chip droplet dispensing with volume control by electro-wetting actuation and capacitance metering", Sensors and Actuators B: Chemical, vol. 98, Mar. 2004, 319-327.
Ren et al., "Design and testing of an interpolating mixing architecture for electrowetting-based droplet-on-chip chemical dilution", Transducers, 12th International Conference on Solid-State Sensors, Actuators and Microsystems, 2003, 619-622.
Ren et al., "Dynamics of electro-wetting droplet transport", Sensors and Actuators B (Chemical), vol. B87, No. 1, Nov. 15, 2002, 201-206.
Ren et al., "Micro/Nano Liter Droplet Formation and Dispensing by Capacitance Metering and Electrowetting Actuation", IEEE—NANO, 2002, 369-372.

(56) References Cited

OTHER PUBLICATIONS

Sherman et al., "Flow Control by Using High-Aspect-Ratio, In-Plane Microactuators", Sensors and Actuators, vol. 73, 1999, pp. 169-175.
Sherman et al., "In-Plane Microactuator for Fluid Control Application", Proc. IEEE Micro Electro Mechanical Systems Workshop, Heidelberg, Germany, Jan. 1998, pp. 454-459.
Sista, "Development of a Digital Microfluidic Lab-on-a-Chip for Automated Immunoassays with Magnetically Responsive Beads", PhD Thesis, Department of Chemical Engineering, Florida State University, 2007.
Srinivasan et al., "3-D imaging of moving droplets for microfluidics using optical coherence tomography", Proc. 7th International Conference on Micro Total Analysis Systems (mTAS), Squaw Valley, CA, Oct. 5-9, 2003, 1303-1306.
Srinivasan et al., "A digital microfluidic biosensor for multianalyte detection", Proc. IEEE 16th Annual Int'l Conf. on Micro Electro Mechanical Systems Conference, 2003, 327-330.
Srinivasan, "A Digital Microfluidic Lab-on-a-Chip for Clinical Diagnostic Applications", Ph.D. thesis, Dept of Electrical and Computer Engineering, Duke University, 2005.
Srinivasan et al., "An integrated digital microfluidic lab-on-a-chip for clinical diagnostics on human physiological fluids", Lab on a Chip, vol. 4, 2004, 310-315.
Srinivasan et al., "Clinical diagnostics on human whole blood, plasma, serum, urine, saliva, sweat and tears on a digital microfluidic platform", Proc. 7th International Conference on Micro Total Analysis Systems (mTAS), Squaw Valley, CA, Oct. 5-9, 2003, 1287-1290.
Srinivasan et al., "Droplet-based microfluidic lab-on-a-chip for glucose detection", Analytica Chimica Acta, vol. 507, No. 1, 2004, 145-150.
Srinivasan et al., "Protein Stamping for MALDI Mass Spectrometry Using an Electrowetting-based Microfluidic Platform", Lab-on-a-Chip: Platforms, Devices, and Applications, Conf. 5591, SPIE Optics East, Philadelphia, Oct. 25-28, 2004.
Srinivasan et al., "Scalable Macromodels for Microelectromechanical Systems", Technical Proc. 2001 Int. Conf. on Modeling and Simulation of Microsystems, 2001, 72-75.
Su et al., "Yield Enhancement of Digital Microfluidics-Based Biochips Using Space Redundancy and Local Reconfiguration", Proc. Design, Automation and Test in Europe (DATE) Conf., IEEE, 2005, 1196-1201.
Sudarsan et al., "Printed circuit technology for fabrication of plastic based microfluidic devices", Analytical Chemistry vol. 76, No. 11, Jun. 1, 2004, Previously published online, May 2004, 3229-3235.
Wang et al., "Droplet-based micro oscillating-flow PCR chip", J. Micromechanics and Microengineering, vol. 15, 2005, 1369-1377.
Wang et al., "Efficient in-droplet separation of magnetic particles for digital microfluidics", Journal of Micromechanics and Microengineering, vol. 17, 2007, 2148-2156.
Xu et al., "A Cross-Referencing-Based Droplet Manipulation Method for High-Throughput and Pin-Constrained Digital Microfluidic Arrays", Proceedings of conference on Design, Automation and Test in Europe (DATE ), Apr. 2007.
Xu et al., "Automated Design of Pin-Constrained Digital Microfluidic Biochips Under Droplet-Interference Constraints", ACM Journal on Emerging Technologies is Computing Systems, vol. 3(3), 2007, 14:1-14:23.
Xu et al., "Defect-Aware Synthesis of Droplet-Based Microfluidic Biochips", IEEE, 20th International Conference on VLSI Design, 2007.
Xu et al., "Droplet-Trace-Based Array Partitioning and a Pin Assignment Algorithm for the Automated Design of Digital Microfluidic Biochips", CODES, 2006, 112-117.
Xu et al., "Integrated Droplet Routing in the Synthesis of Microfluidic Biochips", IEEE, 2007, 948-953.
Xu et al., "Parallel Scan-Like Test and Multiple-Defect Diagnosis for Digital Microfluidic Biochips", IEEE Transactions on Biomedical Circuits and Systems, vol. 1(2), Jun. 2007, 148-158.
Xu et al., "Parallel Scan-Like Testing and Fault Diagnosis Techniques for Digital Microfluidic Biochips", Proceedings of the 12th IEEE European Test Symposium (ETS), Freiburg, Germany, May 20-24, 2007, 63-68.
Xu et al., "Same Reference as IDS 569 A Cross-Referencing-Based Droplet Manipulation Method for High-Throughput and Pin-Constrained Digital Microfluidic Arrays", IEEE, 2007.
Yao et al., "Spot Cooling Using Thermoelectric Microcooler", Proc. 18th Int. Thermoelectric Conf, Baltimore, VA, pp. 256-259, Aug. 1999.
Yi et al., "Channel-to-droplet extractions for on-chip sample preparation", Solid-State Sensor, Actuators and Microsystems Workshop (Hilton Head '06), Hilton Head Island, SC, Jun. 2006, 128-131.
Yi et al., "Characterization of electrowetting actuation on addressable single-side coplanar electrodes", Journal of Micromechanics and Microengineering, vol. 16.,Oct. 2006, 2053-2059.
Yi et al., "EWOD Actuation with Electrode-Free Cover Plate", Digest of Tech. papers,13th International Conference on Solid-State Sensors, Actuators and Microsystems (Transducers '05), Seoul, Korea, Jun. 5-9, 2005, 89-92.
Yi et al., "Geometric surface modification of nozzles for complete transfer of liquid drops", Solid-State Sensor, Actuator and Microsystems Workshop, Hilton Head Island, South Carolina, Jun. 6-10, 2004, 164-167.
Yi, "Soft Printing of Biological Liquids for Micro-arrays: Concept, Principle, Fabrication, and Demonstration", Ph.D. dissertation, UCLA, 2004.
Yi et al., "Soft Printing of Droplets Digitized by Electrowetting", Transducers 12th Int'l Conf. on Solid State Sensors, Actuators and Microsystems, Boston, Jun. 8-12, 2003, 1804-1807.
Yi et al., "Soft Printing of Droplets Pre-Metered by Electrowetting", Sensors and Actuators A: Physical, vol. 114, Jan. 2004, 347-354.
Zeng et al., "Actuation and Control of Droplets by Using Electrowetting-on-Dielectric", Chin. Phys. Lett., vol. 21(9), 2004, 1851-1854.
Zhao et al., "In-droplet particle separation by travelling wave dielectrophoresis (twDEP) and EWOD", Solid-State Sensor, Actuators and Microsystems Workshop (Hilton Head '06), Hilton Head Island, SC, Jun. 2006, 181-184.
Zhao et al., "Micro air bubble manipulation by electrowetting on dielectric (EWOD): transporting, splitting, merging and eliminating of bubbles", Lab on a chip, vol. 7, 2007, First published as an Advance Article on the web, Dec. 4, 2006, 273-280.
Paik, et al., "Heat Transfer Analysis for Adaptive Hot-Spot Cooling of Integrated Circuits using Digital Microfluidics", ASME's IMECE, 2005.
Pamula, "Digital Microfluidics for Lab-on-a-Chip Applications", Emerging CAD Challenges for Biochip Design, Design, Automation, and Test in Europe (DATE), Munich, Germany, 2006.
Pamula, et al., "Microfluidic electrowetting-based droplet mixing", Proceedings, MEMS Conference Berkeley, Aug. 2001, 8-10.
Jie Ding, "System level architectural optimization of semi-reconfigurable microfluidic system," M.S. Thesis, Duke University Dept of Electrical Engineering, 2000.
Jian Gong et al., "Portable digital microfluidics platform with active but disposable Lab-on-Chip," Micro Electro Mechanical Systems, 17th IEEE International Conference on (MEMS), Maastricht, Netherlands, Jan. 25-29, 2004; Piscataway, NJ IEEE, Jan. 25, 2004, pp. 355-358.
Moon, Hyejin, Ph.D., "Electrowetting-on-dielectric microfluidics: Modeling, physics, and MALDI application," University of California, Los Angeles, 2005.
Weaver, "Application of Magnetic Microspheres for Pyrosequencing on a Digital Microfluidic Platform", Department of Electrical and Computer Engineering, Duke University, 2005.
Xu et al., "Digital Microfluidic Biochip Design for Protein Crystallization", IEEE—NIH Life Science Systems and Applications Workshop, LISA, Bethesda, MD, Nov. 8-9, 2007, 140-143.
Yi, et al., "Microfluidics technology for manipulation and analysis of biological cells", Analytica Chimica Acta, vol. 560, 2006, 1-23.
PCT International Preliminary Report on Patentability for PCT/US2008/054134 dated Nov. 17, 2009.
Published Abstract from NIH Grant Project No. DK066956-02.
Published Abstract from NIH Grant Project No. GM072155-02.

(56) References Cited

OTHER PUBLICATIONS

Office Action dated Nov. 6, 2015 from U.S. Appl. No. 13/545,716.
Office Action dated Apr. 24, 2015 from U.S. Appl. No. 13/545,716.
Office Action dated Jul. 10, 2015 from U.S. Appl. No. 13/822,990.
Office Action dated Aug. 17, 2015 from U.S. Appl. No. 13/988,190.
Office Action dated Mar. 26, 2013 from U.S. Pat. No. 8,872,527.
Office Action dated Nov. 26, 2012 from U.S. Pat. No. 8,872,527.
Response to Office Action dated Jul. 24, 2015 from U.S. Appl. No. 13/545,716.
Response to Office Action dated Oct. 8, 2015 from U.S. Appl. No. 13/822,990.
Response to Office Action dated Nov. 17, 2015 from U.S. Appl. No. 13/988,190.
Response to Office Action dated Feb. 18, 2013 from U.S. Pat. No. 8,872,527.
Supplementary EP Search Report and Written Opinion for EP/08/73/0019 dated Oct. 2, 2014.
Merkel et al., "Electric fields in fluidic channels and sensor applications with capacitance", Sensors and Actuators A, Elsevier Sequoia S.A., Lausanne, CH, vol. 80, Mar. 2000, 1-7.
Berggren et al., "Review capacitive biosensors", Electroanalysis, Mar. 2001.

* cited by examiner

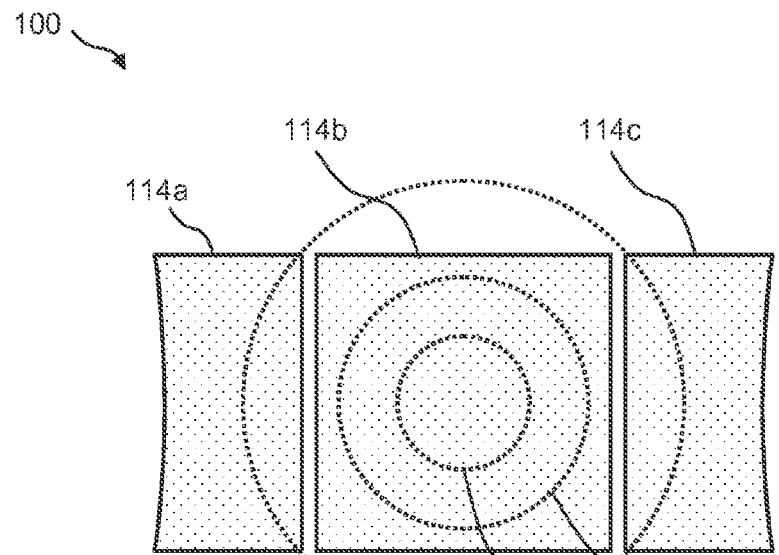
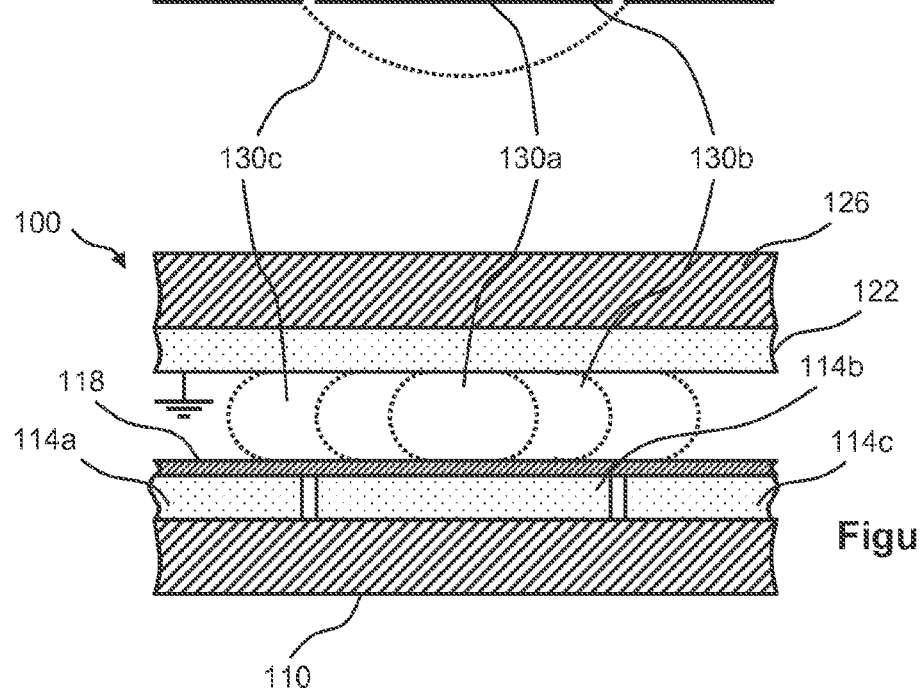
Figure 1A
Figure 1B

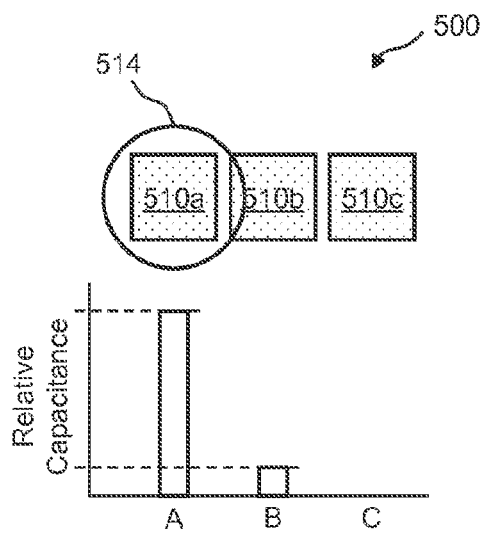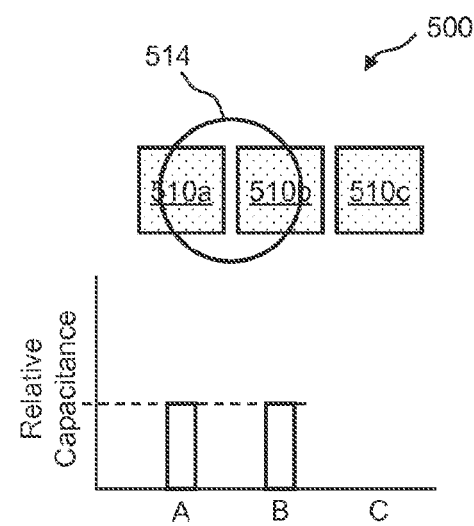
Figure 5A    Figure 5B
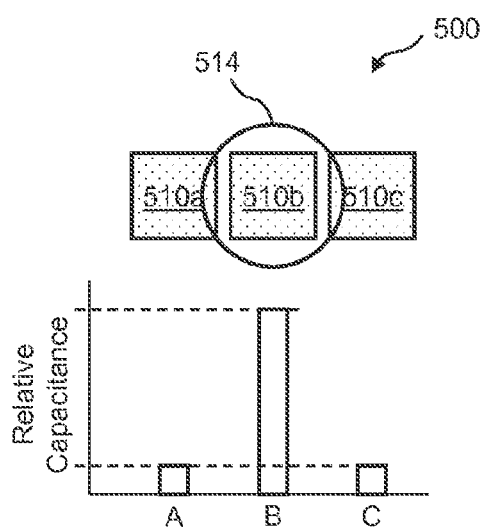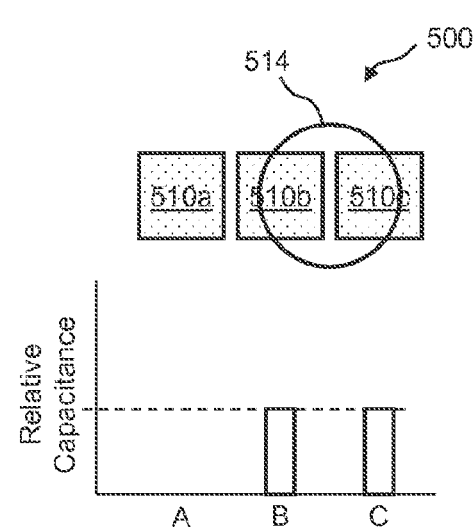
Figure 5C    Figure 5D

CAPACITANCE DETECTION IN A DROPLET ACTUATOR

2 RELATED APPLICATIONS

This application is a continuation of and claims priority to U.S. patent application Ser. No. 12/527,208, filed on Apr. 19, 2010, the application of which is a national stage entry of International Patent Application No. PCT/US2008/054134, filed on Feb. 15, 2008, the application of which claims priority to U.S. Patent Application Nos. 60/980,520, filed on Oct. 17, 2007; 60/980,746, filed on Oct. 17, 2007; and 60/889,966, filed on Feb. 15, 2007 the entire disclosures of which are incorporated herein by reference.

1 GRANT INFORMATION

This invention was made with government support under DK066956, GM072155, and HG003706 awarded by National Institutes of Health. The government has certain rights in the invention.

3 FIELD OF THE INVENTION

The present invention generally relates to the field of conducting droplet operations in a droplet actuator. In particular, the present invention is directed to apparatus and methods for capacitance detection in a droplet actuator.

4 BACKGROUND OF THE INVENTION

Droplet actuators are used to conduct a wide variety of droplet operations. A droplet actuator typically includes two plates separated by a space. The plates include electrodes for conducting droplet operations. The space is typically filled with a filler fluid that is immiscible with the fluid that is to be manipulated on the droplet actuator. A droplet on the droplet actuator is separated from one or more of the electrodes by a dielectric layer. The droplet may be grounded. For a variety of reasons described more fully herein, it may be useful to measure the capacitance of the dielectric layer between the electrode(s) and the droplet.

5 BRIEF DESCRIPTION OF THE INVENTION

The invention provides example methods of performing capacitance detection on a droplet actuator. A capacitor may be formed by the combination of a conductive droplet, an insulator layer, and one or more transport electrodes within a droplet actuator. At any given electrode, the capacitance measured is proportional to the footprint area of a droplet thereon. In some embodiments, the capacitance detection methods described herein may be used as a real-time verification tool in order to detect the absence, presence, and/or partial presence of a droplet at an electrode; analysis of droplet properties; measurement of droplet size or volume; optimization of the speed of droplet operations; and detection of air bubbles.

Additionally, the invention provides a capacitance detection circuit, droplet actuator chips and systems comprising the circuit, and related methods. The circuit is useful for performing capacitance detection its a droplet actuator. Capacitance detection permits analysis of a variety of operations in a droplet actuator. For example, capacitance detection may be used to determine at a designated location whether a droplet is present, partially present or absent. Capacitance at the location will vary depending on the presence, partial presence or absence of the droplet. This capability provides, among other things, a means of verifying whether a certain droplet operation or protocol is progressing as expected. Additionally, by use of existing droplet actuator infrastructures, such as the existing voltage reference electrode of the top plate, which is common to all electrodes of the bottom plate, and the existing droplet actuation control switches, the invention facilitates the use of a single detection circuit for performing capacitance measurements at multiple electrodes.

6 DEFINITIONS

As used herein, the following terms have the meanings indicated.

"Activate" with reference to one or more electrodes means effecting a change in the electrical state of the one or more electrodes which results in a droplet operation.

"Bead," with respect to beads on a droplet actuator, means any bead or particle that is capable of interacting with a droplet on or in proximity with a droplet actuator. Beads may be any of a wide variety of shapes, such as spherical, generally spherical, egg shaped, disc shaped, cubical and other three dimensional shapes. The bead may, for example, be capable of being transported in a droplet on a droplet actuator or otherwise configured with respect to a droplet actuator in a manner which permits a droplet on the droplet actuator to be brought into contact with the bead, an the droplet actuator and/or off the droplet actuator. Beads may be manufactured using a wide variety of materials, including for example, resins, and polymers. The beads may be any suitable size, including for example, microbeads, microparticles, nanobeads and nanoparticles. In some cases, beads are magnetically responsive; in other cases beads are not significantly magnetically responsive. For magnetically responsive beads, the magnetically responsive material may constitute substantially all of a bead or one component only of a bead. The remainder of the bead may include, among other things, polymeric material, coatings, and moieties which permit attachment of an assay reagent. Examples of suitable magnetically responsive beads are described in U.S. Patent Publication No. 2005-0260686, entitled, "Multiplex flow assays preferably with magnetic particles as solid phase," published on Nov. 24, 2005, the entire disclosure of which is incorporated herein by reference for its teaching concerning magnetically responsive materials and beads. The beads may include one or more populations of biological cells adhered thereto. In some cases, the biological cells are a substantially pure population. In other cases, the biological cells include different cell populations, e.g., cell populations which interact with one another.

"Droplet" means a volume of liquid on a droplet actuator that is at least partially bounded by filler fluid. For example, a droplet may be completely surrounded by filler fluid or may be bounded by filler fluid and one or more surfaces of the droplet actuator. Droplets may take a wide variety of shapes; nonlimiting examples include generally disc shaped, slug shaped, truncated sphere, ellipsoid, spherical, partially compressed sphere, hemispherical, ovoid, cylindrical, and various shapes formed during droplet operations, such as merging or splitting or formed as a result of contact of such shapes with one or more surfaces of a droplet actuator.

"Droplet operation" means any manipulation of a droplet on a droplet actuator. A droplet operation may, for example, include: loading a droplet into the droplet actuator; dispensing one or more droplets from a source droplet; splitting, separating or dividing a droplet into two or more droplets; transporting a droplet from one location to another in any direction; merging or combining two or more droplets into a single droplet; diluting a droplet; mixing a droplet; agitating a droplet; deforming a droplet; retaining a droplet in position; incubating a droplet; heating a droplet; vaporizing a droplet; cooling a droplet; disposing of a droplet; transporting a droplet out of a droplet actuator; other droplet operations described herein; and/or any combination of the foregoing. The terms "merge," "merging," "combine," "combining" and the like are used to describe the creation of one droplet from two or more droplets. It should be understood that when such a term is used in reference to two or more droplets, any combination of droplet operations sufficient to result in the combination of the two or more droplets into one droplet may be used. For example, "merging droplet A with droplet B," can be achieved by transporting droplet A into contact with a stationary droplet B, transporting droplet B into contact with a stationary droplet A, or transporting droplets A and B into contact with each other. The terms "splitting," "separating" and "dividing" are not intended to imply any particular outcome with respect to size of the resulting droplets (i.e., the size of the resulting droplets can be the same or different) or number of resulting droplets (the number of resulting droplets may be 2, 3, 4, 5 or more). The term "mixing" refers to droplet operations which result in more homogenous distribution of one or more components within a droplet. Examples of "loading" droplet operations include microdialysis loading, pressure assisted loading, robotic loading, passive loading, and pipette loading.

"Immobilize" with respect to magnetically responsive beads, means that the beads are substantially restrained in position in a droplet or in filler fluid on a droplet actuator. For example, in one embodiment, immobilized beads are sufficiently restrained in position to permit execution of a splitting operation on a droplet, yielding one droplet with substantially all of the beads and one droplet substantially lacking in the beads.

"Magnetically responsive" means responsive to a magnetic field. "Magnetically responsive beads" include or are composed of magnetically responsive materials. Examples of magnetically responsive materials include paramagnetic materials, ferromagnetic materials, ferrimagnetic materials, and metamagnetic materials. Examples of suitable paramagnetic materials include iron, nickel, and cobalt, as well as metal oxides, such as $Fe_3O_4$, $BaFe_{12}O_{19}$, CoO, NiO, $Mn_2O_3$, $Cr_2O_3$, and CoMnP.

"Washing" with respect to washing a bead means reducing the amount and/or concentration of one or more substances in contact with the bead or exposed to the bead from a droplet in contact with the bead. The reduction in the amount and/or concentration of the substance may be partially complete, substantially complete, or even complete. The substance may be any of a wide variety of substances: examples include target substances for further analysis, and unwanted substances, such as components of a sample, contaminants, and/or excess reagent. In some embodiments, a washing operation begins with a starting droplet in contact with a bead, where the droplet includes an initial amount and initial concentration of a substance. The washing operation may proceed using a variety of droplet operations. The washing operation may yield a droplet including the magnetically responsive bead, where the droplet has a total amount and/or concentration of the substance which is less than the initial amount and/or concentration of the substance. Other embodiments are described elsewhere herein, and still others will be immediately apparent in view of the present disclosure. Examples of suitable approaches to washing include, without limitation, those described in U.S. patent application Ser. No. 60/900, 653, filed on Feb. 9, 2007, entitled "Immobilization of magnetically-responsive beads during droplet operations"; Ser. No. 60/980,772, filed on Oct. 17, 2007, entitled "Immobilization of magnetically-responsive beads in droplets"; Ser. No. 60/969,736, filed on Sep. 4, 2007, entitled "Droplet actuator assay improvements"; and Ser. No. 60/980,762, filed on Oct. 17, 2007, entitled "Droplet actuator assay improvements"; and International Patent Application No. International Patent Application No. PCT/US2006/47486, filed on Dec. 11, 2006, entitled "Droplet-Based Biochemistry."

The terms "top" and "bottom" are used throughout the description with reference to the top and bottom substrates of the droplet actuator for convenience only, since the droplet actuator is functional regardless of its position in space.

When a given component, such as a layer, region or substrate, is referred to herein as being disposed or formed "on" another component, that given component can be directly on the other component or, alternatively, intervening components (for example, one or more coatings, layers, interlayers, electrodes or contacts) can also be present. It will be further understood that the terms "disposed on" and "formed on" are used interchangeably to describe how a given component is positioned or situated in relation to another component. Hence, the terms "disposed on" and "formed on" are not intended to introduce any limitation relating to particular methods of material transport, deposition, or fabrication.

When a liquid in any form (e.g., a droplet or a continuous body, whether moving or stationary) is described as being "on", "at", or "over" an electrode, array, matrix or surface, such liquid could be either in direct contact with the electrode/array/matrix/surface, or could be in contact with one or more layers or films that are interposed between the liquid and the electrode/array/matrix/surface.

When a droplet is described as being "on" or "loaded on" a droplet actuator, it should be understood that the droplet is arranged on the droplet actuator in a manner which facilitates using the droplet actuator to conduct one or more droplet operations on the droplet, the droplet is arranged on the droplet actuator in a manner which facilitates sensing of a property of or a signal from the droplet, and/or the droplet has been subjected to a droplet operation on the droplet actuator.

7 BRIEF DESCRIPTION OF THE DRAWINGS

FIGS. 1A and 1B illustrate a top view and side view, respectively, of a droplet actuator;

Figures 6A, 6B:
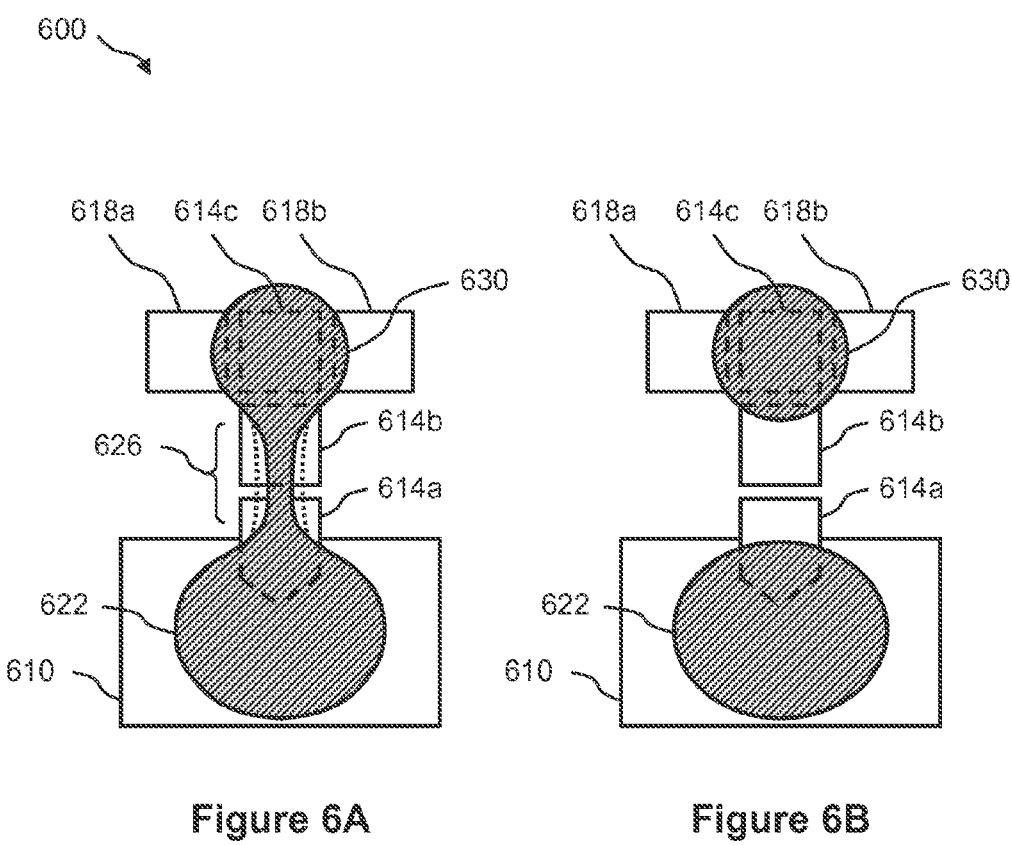
Figure 7:
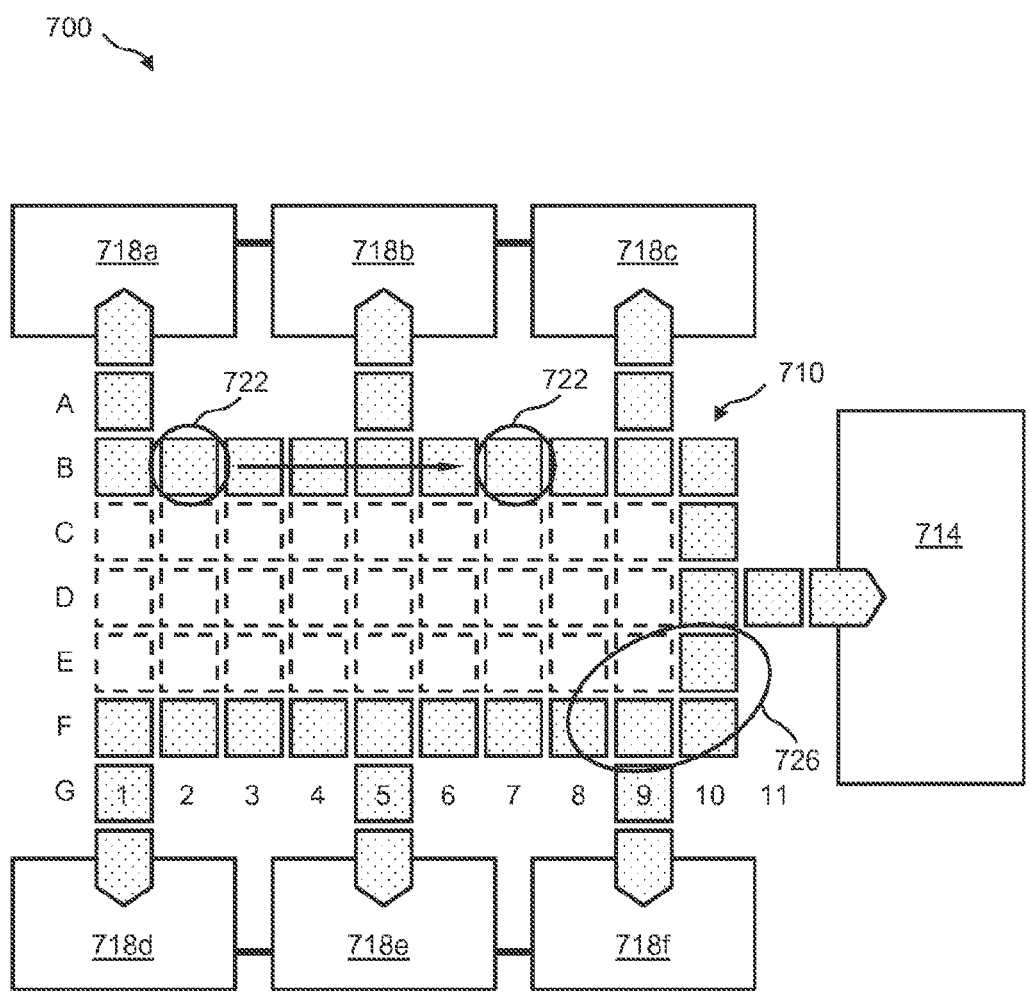
Figure 8:
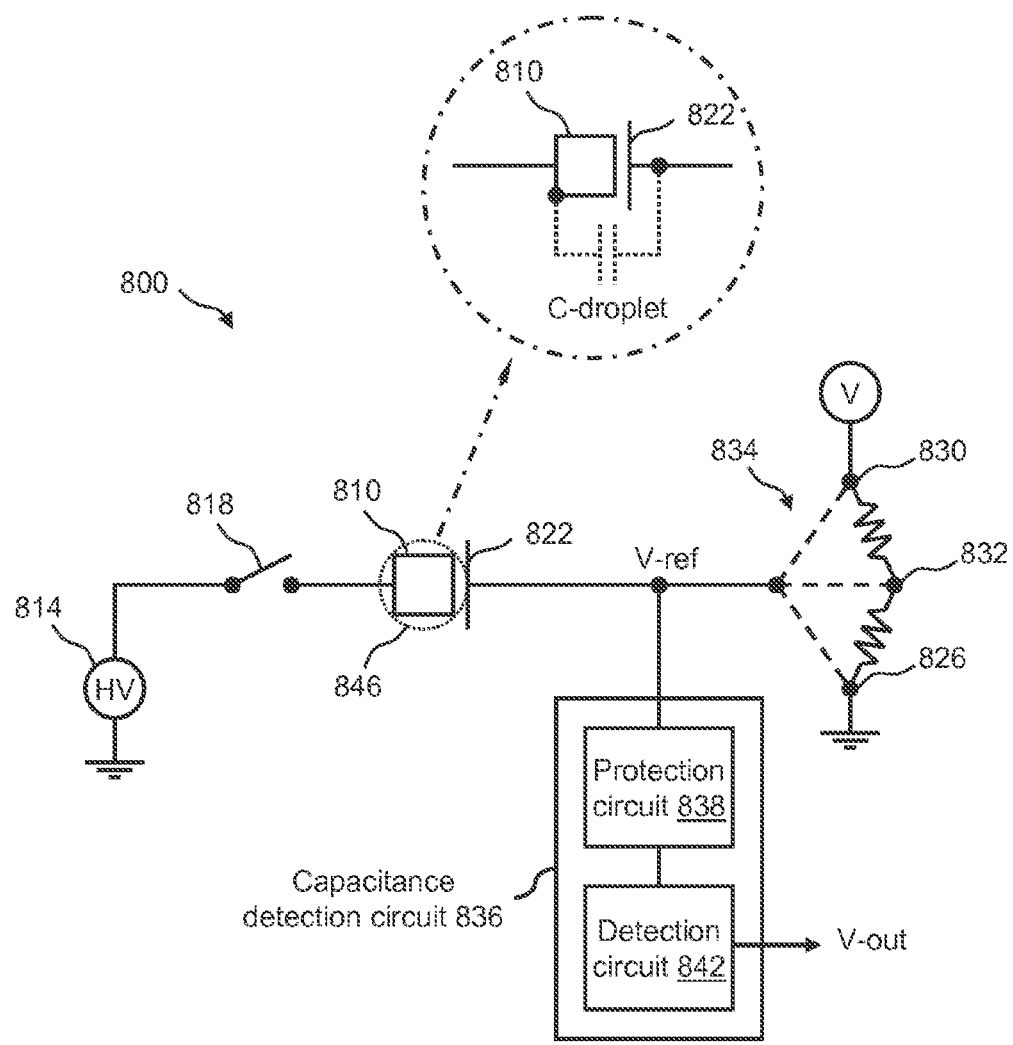
Figure 9:
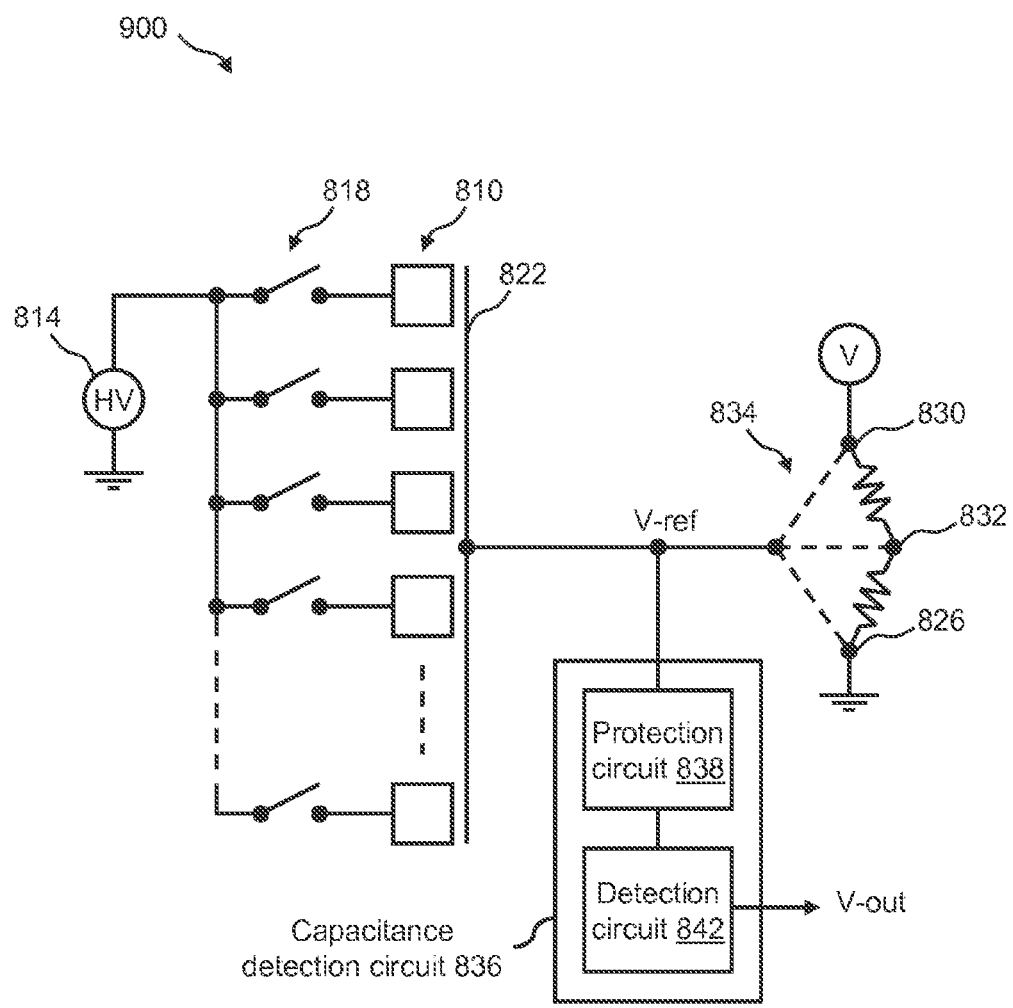
Figure 10A:
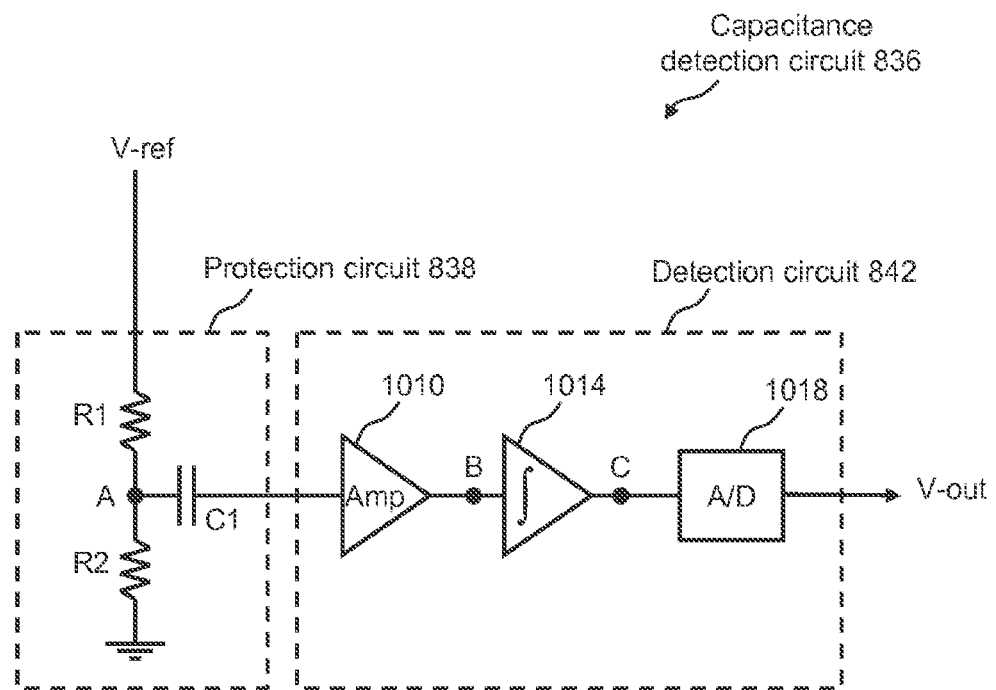
Figure 10B:
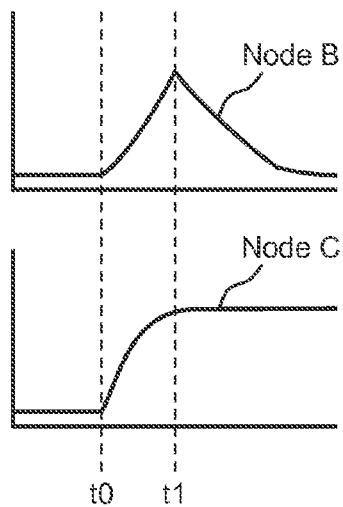

FIGS. 5A, 5B, 5C, and 5D illustrate a nonlimiting example of using capacitance detection in a droplet actuator;

FIGS. 6A and 6B illustrate another nonlimiting example of using capacitance detection in a droplet actuator;

FIG. 7 illustrates yet another nonlimiting example of using capacitance detection in a droplet actuator;

FIG. 8 illustrates a schematic diagram of an embodiment of a droplet actuation circuit of the invention;

FIG. 9 illustrates a schematic diagram of an embodiment of a droplet actuation circuit that includes a capacitance detection circuit;

FIG. 10A illustrates a schematic diagram of an embodiment of a capacitance detection circuit of the invention that may be used in a droplet actuator for the purpose of performing droplet detection; and FIG. 10B illustrates an input voltage curve and an output voltage curve of a charge integrating amplifier that is suitable for use in the capacitance detection circuit of the invention.

8 DETAILED DESCRIPTION OF THE INVENTION

The present invention relates to a droplet actuator configured to detect capacitance of fluids loaded thereon and to methods of making and using such a droplet actuator.

8.1 Capacitance Detection Circuits

FIGS. 1A and 1B illustrate a top view and side view, respectively, of a droplet actuator 100. Droplet actuator 100 includes a first substrate 110, which may be, for example, a glass substrate or a printed circuit board; a plurality of electrodes 114, such as electrodes 114a, 114b, and 114c; an insulator layer 118, which may be, for example, a hydrophobic dielectric layer, and a reference electrode 122 disposed upon a second substrate 126, which may be, for example, a glass substrate. In one example, the plurality of electrodes 114 may include a grid or array of electrodes 114, and the reference electrode 122 may be substantially equidistant from each of the actuator electrodes, wherein the measurement at each of the actuator electrodes in the grid or array may be determined based on the single reference electrode.

A gap between insulator layer 118 and reference electrode 122 forms a fluid path through which one or more droplets of various size and/or footprint may flow. A droplet positioned in the gap between insulator layer 118 and reference electrode 122 at the position of electrode 114b displaces a portion of the filler fluid (e.g. air, silicone oil) that would otherwise occupy that space and therefore results in a change in capacitance measured between electrode 114b and reference electrode 122. A non-conductive droplet results in a change in measured capacitance if the dielectric properties of the droplet differ from the medium being displaced. For example, an oil droplet displacing air filler within the gap at the position of electrode 114b would result in an increased measured capacitance because the dielectric constant of oil is typically higher than air. Similarly, the introduction of an air bubble at the position of electrode 114b when the actuator is filled with oil would reduce the capacitance measured between electrode 114b and reference electrode 122. Because the capacitance contributed by the combination of droplet/bubble/filler within the gap is arranged in series with the capacitance contributed by solid dielectric 118, the relative magnitude of the change in capacitance would depend on the properties of dielectric 118 as well as any other capacitances is the system. It is also noted that presence of filler liquid trapped between the droplet and either of the actuator surfaces could also affect the measured capacitance.

When the droplet positioned between electrode 114b and reference 122 is substantially conductive and is in electrical communication with reference 122, then another capacitive effect is observed. In this case, the droplet effectively "shorts-out" the capacitor formed by the filler liquid between the surface of dielectric 118 and reference 122. That is, the capacitive contribution of the liquid layer at the position of the droplet is effectively reduced such that the dielectric 118 contributes substantially all of the capacitance measured between electrode 114b and reference 122 at the position of the droplet. The capacitance associated with the overlap of the droplet and electrode is arranged in parallel with the capacitance associated with the portions of electrode 114b not overlapping the droplet and being covered with filler fluid. There is a certain amount of capacitance associated with the droplet fully covering the electrode and a certain amount of capacitance associated with the droplet being fully absent from the electrode. Between these two extremes the amount of capacitance measured is proportional to the amount of overlap between the droplet and electrode. Although fringing electrical fields exist at the electrode edges, in most cases the contribution of these fields can be neglected so the measured capacitance is directly proportional to the amount of overlap. The total amount of area included in the overlap between the base of the droplet and the surface of the dielectric at the position of an electrode is referred to as the footprint of the droplet.

In one example, FIGS. 1A and 1B show a droplet 130a that is fully contained within the lateral extent of electrode 114b and that forms a certain footprint on electrode 114b; droplet 130b that is of a certain larger footprint than droplet 130a and which has a size that is roughly proportional to the size of electrode 114b; and droplet 130c that is of a certain larger footprint than both droplets 130a and 130b and is atop electrode 114b and overlaps onto adjacent electrodes 114a and 114c.

The combination of an insulator layer that is arranged between a conductive droplet, which may be connected to a reference potential, and another conductive layer effectively forms a parallel plate capacitor. More specifically and referring again to FIGS. 1A and 1B, insulator layer 118, which is the dielectric layer, is arranged between droplet 130a, 130b, or 130c, which has a certain amount of electrical conductivity, and one or more electrodes 114, thereby forming a plate capacitor. Droplet 130a, 130b, or 130c may be electrically connected to a reference electrode 122 and electrodes 114 may be electrically connected to a bias voltage. It is further understood that in other embodiments, the reference electrode can be in a co-planar relationship with the electrodes.

The amount of capacitance C-droplet measured due to the presence or absence of a droplet is a function of the droplet footprint area on that electrode. Because capacitance $C=\in(A/d)$; where C is the capacitance in farads, F; $\in$ is the permittivity of the insulator used; A is the area of each plate (in square meters); and d is the separation between the plates (in meters). Therefore and referring again to FIGS. 1A and 1B, the area of the footprint of droplet 130c on electrode 11b>the area of the footprint of droplet 130b on electrode 114b>the area of the footprint of droplet 130a on electrode 114b and, thus, the capacitance measured between droplet 130c and electrode 114b>the capacitance measured between droplet 130b and electrode 114b>the capacitance measured between droplet 130a and electrode 114b.

In the situation where a fluid droplet is located over the actuator electrode, a processor, for example, can initiate a measurement of an amount by which a portion of the droplet overlaps the actuator electrode.

Figure 2:
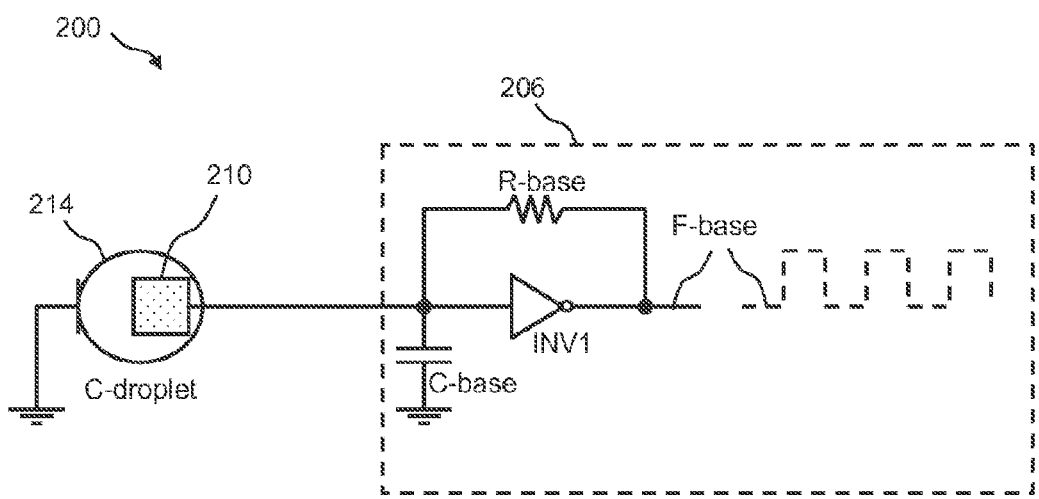
FIG. 2 illustrates a nonlimiting example of a capacitance detection circuit for determining C-droplet.

FIG. 2 illustrates a nonlimiting example of a capacitance detection circuit 200 for determining C-droplet. In particular, capacitance detection circuit 200 performs an active capacitance measurement by providing a reference signal that is applied to an electrode.

For example, capacitance detection circuit 200 includes a ring oscillator circuit 206 that is formed of an inverter INV1 in combination with a base resistance R-base and a base capacitance C-base, which are arranged as shown in FIG. 2. Resistance R-base and capacitance C-base form an RC circuit that determines a base oscillation frequency F-base. The input of ring oscillator circuit 206 is electrically connected to an electrode 210 upon which may be disposed on droplet 214, which may be connected to a reference potential. The droplet, such as droplet 214, controls a certain capacitance C-droplet between sensing electrode 210 and the reference potential that is in parallel with capacitance C-base. Consequently the capacitance C-droplet adds to capacitance C-base, which controls the frequency F-base. A change in frequency F-base, which is the result of a change in capacitance C-droplet due to motion of the droplet 210, may be measurable by, for example, a pulse counter (not shown) that is connected to the output of ring oscillator circuit 206. The change in frequency F-base is inversely proportional to the change in capacitance C-droplet, i.e., the frequency F-base decreases as capacitance C-droplet increases. By calculating the difference between frequency F-base with and without the droplet present, a capacitance value may be determined, which may be correlated to the absence, presence, and/or partial presence of, for example, droplet 214 at electrode 210. Note that in this example, electrode 210 may be either biased or unbiased during the capacitance measurement.

Figure 3:
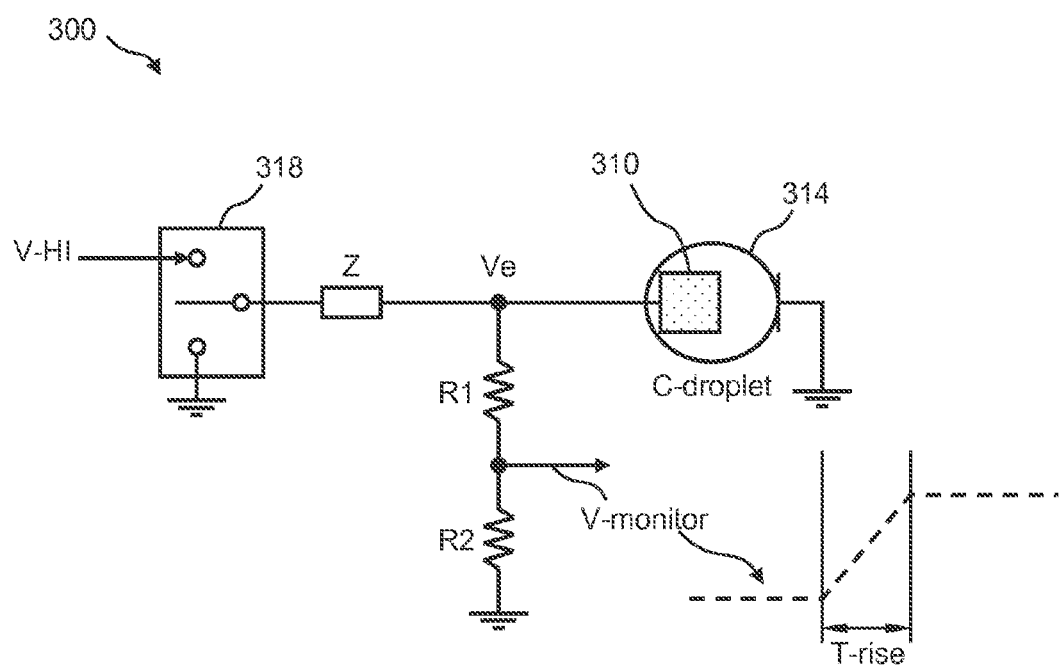
FIG. 3 illustrates another nonlimiting example of a capacitance detection circuit for determining the capacitance of a droplet within a droplet actuator.

FIG. 3 illustrates another nonlimiting example of a capacitance detection circuit 300 for determining the capacitance of a droplet within a droplet actuator. In particular, capacitance detection circuit 300 performs a passive capacitance measurement by monitoring the charge time of capacitance C-droplet. For example, capacitance detection circuit 300 includes a transport electrode 310 upon which may be disposed a droplet 314, which may be grounded. When droplet 314 is fully or partially present it has a capacitance C-droplet. The control line of transport electrode 310 has a certain impedance Z and may be connected to either a bias voltage V-HI or to ground via a switch 318. Switch 318 may be any electronic switch mechanism.

When droplet 314 is fully or partially present, capacitance C-droplet is charged when transport electrode 310 is connected to bias voltage V-HI. By contrast, capacitance C-droplet is discharged when transport electrode 310 is connected to ground. As electrode voltage Ve, which may be a high voltage, at transport electrode 310 may be monitored by use of a voltage divider circuit, in order to provide a low voltage monitor. In one example, a resistor R1 and R2 are arranged in series between electrode voltage Ve and ground, and a voltage V-monitor is provided at a node between resistors R1 and R2. A rise time T-rise of voltage V-monitor when transport electrode 310 is switched from ground to bias voltage V-HI may be monitored. Consequently, when droplet 314 is fully or partially present at transport electrode 310, the capacitance C-droplet that is introduced causes the rise time T-rise of voltage V-monitor to increase. The change in T-rise, which is the result of introducing capacitance C-droplet, may be measurable by, for example, an analog-to-digital (A/D) converter (not shown) that is connected to voltage V-monitor. The change in T-rise at voltage V-monitor is proportional to the amount of capacitance C-droplet, i.e., T-rise increases as capacitance C-droplet increases. By calculating the difference between T-rise at voltage V-monitor with and without capacitance C-droplet present, a capacitance C-droplet value may be determined, which may be correlated to the absence, presence, and/or partial presence of, for example, droplet 314 at transport electrode 310.

Figure 4:
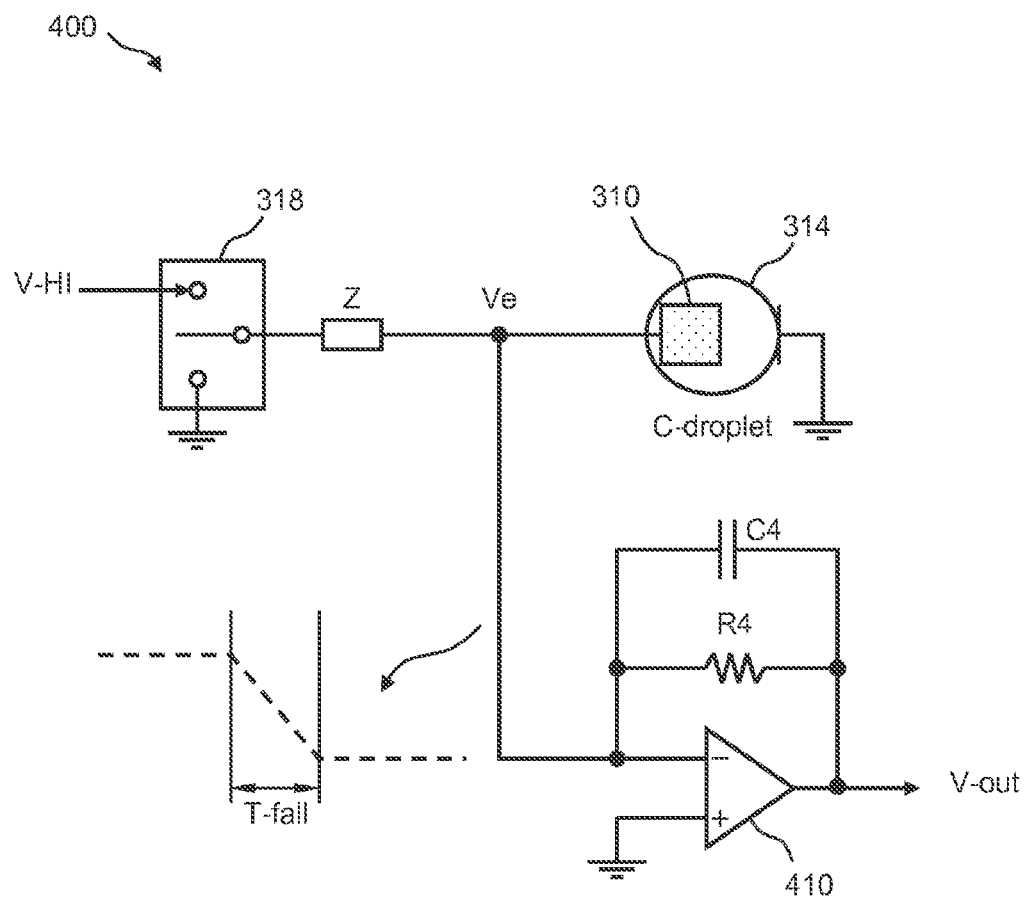
FIG. 4 illustrates yet another nonlimiting example of a capacitance detection circuit for determining the capacitance of a droplet within a droplet actuator.

FIG. 4 illustrates yet another nonlimiting example of a capacitance detection circuit 400 for determining the capacitance of a droplet within a droplet actuator. In particular, capacitance detection circuit 400 performs a passive capacitance measurement by monitoring the discharge time of capacitance C-droplet. For example, capacitance detection circuit 400 is substantially the same as capacitance detection circuit 300 of FIG. 3 except that it does not include a voltage divider circuit. Instead, electrode voltage Ve of capacitance detection circuit 400 is monitored directly via a charge integrating amplifier 410, which outputs a voltage V-out that is the integral of its input voltage. However, alternatively, the elements of capacitance detection circuit 300 and capacitance detection circuit 400 may be combined.

Transport electrode 310 is first connected to bias voltage V-HI via switch 318 for a period of time that allows capacitance C-droplet to be fully charged to a certain voltage. After capacitance C-droplet is fully charged, transport electrode 310 is then connected to ground via switch 318, which discharges capacitance C-droplet and, thus, electrode voltage Ve falls from the certain voltage to ground with a fall time of T-fall. Consequently, when droplet 314 is fully or partially present at transport electrode 310, the capacitance C-droplet that is introduced causes the fall time T-fall of electrode voltage Ve to increase. The integral of T-fall may be analyzed at V-out of charge integrating amplifier 410 by, for example, an A/D converter (not shown). The change in T-fall of electrode voltage Ve is proportional to the amount of capacitance C-droplet, i.e., T-fall increases as capacitance C-droplet increases. By calculating the difference between T-fall of electrode voltage Ve with and without capacitance C-droplet present, a capacitance C-droplet value may be determined, which may be correlated to the absence, presence, and/or partial presence of, for example, droplet 314 at transport electrode 310.

8.2 Uses of Capacitance Detection

Capacitance detection in a droplet actuator can be employed to affect a variety of useful results. Examples follow.

8.2.1 Analysis of Basic Microfluidic Functions

FIGS. 5A, 5B, 5C, and 5D illustrate a nonlimiting example of using capacitance detection in a droplet actuator. More specifically, FIGS. 5A, 5B, 5C, and 5D illustrate a set of nonlimiting exemplary steps of a droplet operation process 500, which demonstrates a simple inexpensive analysis of basic microfluidic functions by use of capacitance detection. In particular, FIGS. 5A, 5B, 5C, and 5D show the real-time progression of an exemplary droplet 514 moving along a line of transport electrodes 510, such as transport electrodes 510a, 510b, and 510c. In this example, each of transport electrodes 510a, 510b, and 510c are connected to a capacitance detection mechanism, such as, but not limited to, capacitance detection circuit 200 of FIG. 2, capacitance detection circuit 300 of FIG. 3, and capacitance detection circuit 400 of FIG. 4, for measuring the capacitance C-droplet. In doing so, the absence, presence, partial presence, and/or location of droplet 514 along the line of transport electrodes 510 may be determined in real time. For each step shown by FIGS. 5A, 5B, 5C, and 5D, respectively, a bar graph of the relative capacitance C-droplet at each of transport electrodes 510a, 510b, and 510c is provided.

FIG. 5A shows droplet 514 at a first location along the line of transport electrodes 510a, 510b, and 510c. More specifically, droplet 514 is centered open transport electrode 510a and shows that the footprint area of droplet 514 is larger than the area of transport electrode 510a. Therefore, while droplet 514 is centered upon transport electrode 510a, it also overlaps slightly the adjacent transport electrode 510b. The bar graph for FIG. 5A of the relative amount of capacitance C-droplet shows that maximum capacitance C-droplet is detected at transport electrode 510a, a small capacitance C-droplet is detected at transport electrode 510b, and no capacitance C-droplet detected at transport electrode 510c. As a result, without the need for visualization, it may be concluded that the location of droplet 514 is substantially at transport electrode 510a.

FIG. 5B shows droplet 514 at a second location along the line of transport electrodes 510a, 510b, and 510c. More specifically, droplet 514 is bridging transport electrodes 510a and 510b. Therefore, a substantially equal portion of droplet 514 is upon each of transport electrodes 510a and 510b. The bar graph for FIG. 5B of the relative amount of capacitance C-droplet shows that approximately half the maximum capacitance C-droplet is detected at each of transport electrodes 510a and 510b and no capacitance C-droplet is detected at transport electrode 510c. As a result, without the need for visualization, it may be concluded that the movement of droplet 514 from transport electrode 510a to 510b is progressing as expected.

FIG. 5C shows droplet 514 at a third location along the line of transport electrodes 510a, 510b, and 510c. More specifically, droplet 514 is centered upon transport electrode 510b and shows that the footprint area of droplet 514 is larger than the area of transport electrode 510b. Therefore, while droplet 514 is centered upon transport electrode 510b, it also overlaps slightly the adjacent transport electrodes 510a and 510c. The bar graph for FIG. 5C of the relative amount of capacitance C-droplet shows that a small amount of capacitance C-droplet is detected at transport electrode 510a, maximum capacitance C-droplet is detected at transport electrode 510b, and a small amount of capacitance C-droplet is detected at transport electrode 510c. As a result, without the need for visualization, it may be concluded that the movement of droplet 514 to substantially the position of transport electrode 510b has occurred as expected.

FIG. 5D shows droplet 514 at a fourth location along the line of transport electrodes 510a, 510b, and 510c. More specifically, droplet 514 is bridging transport electrodes 510b and 510c. Therefore, a substantially equal portion of droplet 514 is upon each of transport electrodes 510b and 510c. The bar graph for FIG. 5D of the relative amount of capacitate C-droplet shows that no capacitance C-droplet is detected at transport electrode 510a and approximately half the maximum capacitance C-droplet is detected at each of transport electrodes 510b and 510c. As a result, without the need for visualization, it may be concluded that the movement of droplet 514 from transport electrode 510b to 510c is progressing as expected.

8.2.2 Droplet Splitting Operations

FIGS. 6A and 6B illustrate another nonlimiting example of using capacitance detection in a droplet actuator. More specifically, FIGS. 6A and 6B illustrate a nonlimiting example of a droplet actuator 600 that uses capacitance detection in a droplet splitting operation for determining droplet uniformity. In particular, FIG. 6A shows the droplet splitting operation in progress and FIG. 6B shows the droplet splitting operation when complete. Droplet actuator 600 includes a reservoir electrode 610 that outlets to a line of transport electrodes 614a, 614b, and 614c. Adjacent to and on either side of transport electrode 614c is a transport electrode 618a and 618b. In this example, each of transport electrodes 614a, 614b, 614c, 618a and 618b are connected to a capacitance detection mechanism, such as, but not limited to, capacitance detection circuit 200 of FIG. 2, capacitance detection circuit 300 of FIG. 3, and capacitance defection circuit 400 of FIG. 4, for detecting the capacitance C-droplet.

Referring again to FIGS. 6A and 6B, a volume of fluid 622 is provided at reservoir electrode 610. During the droplet splitting operation, transport electrode 614c is activated and fluid 622 from reservoir electrode 610 is pinched off across a split zone 626 along transport electrodes 614a and 614b to form a droplet 630 at transport electrode 614c. The size of droplet 630 may vary, for example, because as the volume of fluid 622 at reservoir electrode 610 varies, the amount of fluid pinched off may vary. However, capacitance detection may be used in order to monitor the droplet splitting operation and provide uniform droplet dispensing. For example, by applying capacitance detection at transport electrode 614c and transport electrode 618a and transport electrode 618b the relative position and distribution of the liquid across each electrode may be determined. The progression of fluid 622 as it flows across portions of transport electrode 614a, transport electrode 614b, transport electrode 614c, transport electrode 618a and transport electrode 618b may be monitored in realtime. Similarly, as transport electrode 614a and transport electrode 614b are deactivated, the progression of the fluid as it drains back to reservoir electrode 610 can similarly be determined. Based on this, the size of droplet 630 may be determined and adjustments to the process may be performed in order to ensure a reproducible droplet geometry at transport electrode 614c. Additionally, by applying capacitance detection at reservoir electrode 610 and transport electrode 614a and 614b the volume of fluid at reservoir electrode 610 and at split zone 626 may be determined and adjustments to the process may be performed in order to ensure a reproducible droplet geometry at transport electrode 614c. For example, if droplet 630 is too small, certain actions or adjustments to the droplet operation process may be performed, such as, but not limited to, returning the droplet to the reservoir, adding more volume to reservoir, adjusting the electrode bias voltage, adjusting the electrode bias time, and any combinations thereof. Adjustments may also be made in real-time as the droplet splitting process in being performed based on capacitance-based feedback from each of the electrodes participating in the process. For example, the amount of voltage on a particular electrode could be adjusted to maintain a particular rate of liquid drainage or certain electrodes could activated or deactivated at particular times depending on the location of the liquid and progression of the droplet splitting process.

8.2.3 Droplet Transport Fault Detection

FIG. 7 illustrates yet another nonlimiting example of using capacitance detection in a droplet actuator. More specifically, FIG. 7 illustrates a nonlimiting example of a droplet actuator 700 that uses capacitance detection in a droplet transport fault detection application and/or a quality control application. Droplet actuator 700 includes a set of transport electrodes that are arranged, for example, in a grid. In one example, droplet actuator 700 includes an array of transport electrodes 710 that are arranged along rows A through G and columns 1 through 11 and that are in fluid connection with a reservoir 714 and multiple receptacles 718, such as receptacles 718a through 718f. In this example, all or certain selected transport electrodes 710 are connected to a capacitance detection mechanism, such as, but not limited to, capacitance detection circuit 200 of FIG. 2, capacitance defection circuit 300 of FIG. 3, and capacitance detection circuit 400 of FIG. 4, for detecting the droplet capacitance C-droplet.

Referring again to FIG. 7, in a droplet transport fault detection application, capacitance detection may be used for determining whether an electrode has failed (e.g., due to open electrical connection). More specifically, capacitance detection may be used to monitor the flow within droplet actuator 700. In one example, FIG. 7 shows a droplet 722 moving from, for example, grid location B2 to B7. If the expected change in capacitance is not measured at a certain selected transport electrode 710 along the path, a fault is detected, which may prompt certain action, such as, but not limited to, routing droplet 722 from grid location B2 to B7 via an alternate path. In one example, when a droplet transport fault is detected along the path from grid location B2 to B7, droplet 722 may be alternatively routed from grid location B2 to C2, then from C2 to C7, then from C7 to B7.

Referring again to FIG. 7, in a quality control application at the time of manufacture or operation of the device, when filling with oil the fluid path within a droplet actuator, such as within droplet actuator 700, the presence of air bubbles may be determined using capacitance detection. In one example, FIG. 7 shows an air bubble 726 that is trapped within droplet actuator 700 near one or more transport electrodes 710, which is problematic. Analyzing the capacitance profile of each transport electrode 710 in oil may provide an indication of whether an air bubble is present and its position and extent within the droplet actuator. When a bubble is detected, the device may be reloaded with oil to remedy the problem.

In another quality control application at the time of manufacture, a droplet actuator, such as droplet actuator 700, may be filled with a conductive fluid, such as water. Then the capacitance profile of each transport electrode 710 in a conductive fluid may be analyzed in order to determine whether the capacitance profile for each transport electrode 710 matches an expected capacitance profile. In this way, an open transport electrode 710 or a shorted transport electrode 710 may be detected.

8.2.4 Droplet Transport Speed Detection

Capacitance detection of the presence, absence or partial presence of a droplet at the position of a particular electrode may be used as a basis for measuring the speed of droplet transport in a droplet actuator. Position measurements made at different points in time can be used to calculate the average velocity of droplet motion in a particular interval. For example, a signal may be sent to activate an electrode adjacent to a droplet and the time required for the droplet to move onto that activated electrode may be determined by monitoring the capacitance at that electrode over time due to the footprint of the droplet. Certain threshold levels of capacitance may be defined to facilitate measurements of this type. For example, one could define a transport time based on the time required for the capacitance to change from 10% to 90% where 0% represents the minimum footprint value and 100% represents the maximum footprint value. Many other types of measurements of instantaneous or average droplet position, velocity or acceleration may likewise be made. Furthermore, the measurement need not be made on the activated receiving electrode, but could be made on the deactivated source electrode (i.e. the rate at which the droplet moves away from the source is determined) or could made using a third electrode. For example, the time required for the droplet to traverse an activated electrode and to overlap the next adjacent electrode to a could be measured.

8.3 Additional Examples of Capacitance Detection Architectures

FIG. 8 illustrates a schematic diagram of an embodiment of a droplet actuation circuit 800 of the invention. Droplet actuation circuit 800 includes a capacitance defection circuit and may be used for performing a capacitance measurement at any electrode of a droplet actuator, e.g., for performing droplet detection. Droplet actuation circuit 800 may include an electrode 810, e.g., droplet actuation electrode, for performing droplet operations. Electrode 810 is electrically connected to a high-voltage supply 814, e.g., at an electrowetting voltage, via an electronic switch 818. Electronic switch 818 may be the droplet actuation switch for connecting/disconnecting the voltage of high-voltage supply 814 to/from electrode 810. Electrode 810, high-voltage supply 814, and electronic switch 818 may in some embodiments be associated with the bottom plate (not shown) of a droplet actuator (not shown). Additionally, the droplet actuator may have arrays and/or paths of electrodes 810 for performing droplet operations. FIG. 9, described hereinbelow, illustrates additional details of a droplet actuation circuit that includes multiple electrodes.

Droplet actuation circuit 800 further includes a reference electrode 822 that may be electrically connected to multiple nodes via an electronic switch. In one example, reference electrode 822 may be electrically connected to a ground node 826, a voltage node 830, or a high-impedance node 832 via an electronic switch 834, e.g., a 10 position electronic switch. Reference electrode 822, ground node 826, voltage node 830, high-impedance node 832, and electronic switch 834 may in some embodiments be associated with the top plate (not shown) of a droplet actuator. When reference electrode 822 is electrically connected to ground node 826, it serves as a ground reference plane for the droplet actuator. When reference electrode 822 is electrically connected to voltage node 830, it serves as a voltage reference plane for the droplet actuator. When reference electrode 822 is electrically connected to high-impedance node 832, it is substantially disconnected from ground node 826 and voltage node 830 and is, thus, considered in a "float" state.

The combination of electrode 810, high-voltage supply 814, electronic switch 818, reference electrode 822, ground node 826, voltage node 830, high-impedance node 832, and electronic switch 834 is included in the typical infrastructure of a droplet actuator. However, in addition to these typical elements of a droplet actuator, the invention provides a capacitance detection circuit 836 that includes a protection circuit 838 and a detection circuit 842. More specifically, a voltage, V-ref, at reference electrode 822 is electrically connected to an input of protection circuit 838 of capacitance detection circuit 836. An output of protection circuit 838 is electrically connected to an input of detection circuit 842 of capacitance detection circuit 836. An output voltage, V-out, of detection circuit 842 is provided for monitoring by external resources (not shown). Protection circuit 838 is provided to protect detection circuit 842 from damage due to high voltage when electronic switch 834 is connected to voltage node 830.

FIG. 8 also shows that when a droplet 846 is present at electrode 820, the droplet 846 has certain capacitance, C-droplet, between electrode 810 and reference electrode 822. By contrast, when droplet 846 is not present at electrode 810, capacitance, C-droplet, does not exist between electrode 810 and reference electrode 822.

In operation, during droplet operations, reference electrode 822 may be electrically connected, for example, to ground node 826 via electronic switch 834 and droplet operations may occur at electrode 810 under the control of electronic switch 818. However, during droplet detection operations, reference electrode 822 is electrically connected to high-impedance node 832 via electronic switch 834, to place reference electrode 822 in a "float" state. Additionally, electronic switch 818 that is associated with electrode 810 serves as a rising edge generator. More specifically, a rising edge at electrode 810 is generated by toggling electronic switch 818 from an open state to a closed state, thereby causing a voltage transition to occur at electrode 810 from about 0 volts to about the value of high-voltage supply 814. In this way, the capacitive energy that is caused by the presence of capacitance, C-droplet, of droplet 846 at electrode 810 is coupled to reference electrode 822, which then is coupled to protection circuit 838 and passed to detection circuit 842 of capacitance detection circuit 836. This capacitive energy generated is a voltage pulse at V-ref that is proportional to the capacitance, C-droplet.

The voltage pulse that is present at the V-ref node, which may be a high voltage pulse, is processed via protection circuit 838 and detection circuit 842 of capacitance detection circuit 836 to provide a digital V-out value that reflects the magnitude of capacitance, C-droplet. In one example, when the digital V-out value of detection circuit 842 is about 0 volts, this indicates that there is no droplet 846 present at electrode 810. In another example, when the digital V-out value of detection circuit 842 is a certain expected value that is greater than about 0 volts, this indicates that droplet 846 is present at electrode 810. In this way, capacitance detection circuit 836 provides a way to detect the presence or absence of a droplet at a certain electrode by detecting the presence or absence of capacitance, C-droplet. FIGS. 10A and 10B, described hereinbelow, illustrate more details of an example capacitance detection circuit that includes a detection circuit and a protection circuit.

FIG. 9 illustrates a schematic diagram of an embodiment of a droplet actuation circuit 900 that includes a capacitance detection circuit. The capacitance detection circuit may, for example, be used for a capacitance measurement at any electrode of a droplet actuator, e.g., for performing droplet detection. Droplet actuator circuit 900 is substantially the same as droplet actuator circuit 800 of FIG. 8, except for the illustration of multiple electrodes 810 and the associated bank of electronic switches 818. FIG. 9 shows that all electronic switches 818 are connected to a common high voltage of high-voltage supply 814. In this example, a rising edge may be generated by activating the electronic switch 818 that is associated with an electrode 810 of interest and capacitance detection circuit 836 may be used to detect the presence or absence of capacitance, C-droplet, at the electrode 810 of interest. A sequential operation may occur, i.e., sequencing from one electrode 810/electronic switch 818 pair to the next, by which capacitance detection takes place from one electrode 810 to the next.

FIG. 10A illustrates a schematic diagram of an embodiment of a capacitance detection circuit, such as capacitance detection circuit 836, of the invention that may be used in a droplet actuator for the purpose of performing droplet detection. Capacitance detection circuit 836 includes protection circuit 838 and detection circuit 842. More specifically, the input of protection circuit 838 is fed, for example, by voltage V-ref of droplet actuator circuit 800 or 900 of FIG. 8 or 9, respectively. The output of protection circuit 838 feeds the input of detection circuit 842, which provides a digital V-out value.

Additionally, protection circuit 838 of capacitance detection circuit 836 includes a voltage divider network, such as a resistor R1 and R2 that are electrically connected in series, as shown in FIG. 10A. A voltage node A between resistor R1 and R2 is electrically connected to one side of a capacitor C1. The opposite side of capacitor C1 is electrically connected to the input of detection circuit 842. Because of the action of the voltage divider network, which is formed by resistors R1 and R2, a fraction of the voltage value of V-ref is present at voltage node A. The values of resistors R1 and R2 are such that a suitably safe, low-voltage at node A feeds the input of detection circuit 842, to ensure that a high voltage at V-ref does not damage the components of detection circuit 842. Additionally, capacitor C1 provides an alternating current (AC) coupling mechanism for coupling the AC components only of V-ref to detection circuit 842.

Additionally, detection circuit 842 of capacitance detection circuit 836 includes an amplifier 1010, a charge integrating amplifier 1014, and an analog-to-digital (A/D) converter 1018, which are electrically connected as shown in FIG. 10A. Amplifier 1010 may, for example, be a conventional operational amplifier device that scales its input voltage either up or down to any suitable voltage for feeding the next signal processing stage, the charge integrating amplifier 1014. Alternatively, amplifier 1010 may serve as a buffer only, to convert the input signal impedance to a certain impedance value that is suited to pass to the next signal processing stage, charge integrating amplifier 1014. Charge integrating amplifier 1014 may, for example, be a conventional charge integrating amplifier that generates an output voltage (e.g., voltage node C) that is the integral of its input voltage (e.g., voltage node B), which is illustrated in FIG. 10B. A reason for integrating the output of amplifier 1010 is to render the signal less sensitive to stray capacitances that may be present at electrode 810, while still capturing the capacitance across droplet 846. A/D convener 1018 may, for example, be a conventional n-bit A/D converter device for converting an analog input voltage to an n-bit digital word. For example, A/D converter 1018 may be an 8-bit, 10-bit, or 16-bit A/D converter, depending on a desired resolution.

Referring again to FIGS. 8, 9, 10A, and 10B, the operation of capacitance detection circuit 836 may be summarized as follows. Reference electrode 822 is electrically connected to high-impedance node 832 via electronic switch 834, to place reference electrode 822 in a "float" state, which provides electrical isolation from ground node 826 and voltage node 830 via a high resistance (e.g., Megaohms). For an electrode 810 of interest, its associated electronic switch 818 is toggled from open to closed to generate a rising edge at the electrode 810 of interest. Assuming a droplet 846 is present at the electrode 810 of interest, capacitive energy is coupled to reference electrode 822 that is proportional to capacitance, C-droplet. Protection circuit 838 of capacitance detection circuit 836 reduces the amplitude of V-ref to a suitably low voltage via resistors R1 and R2. Capacitor C1 then couples the low-voltage pulse at node A to amplifier 1010, which scales the low-voltage pulse to any usable value for feeding charge integrating amplifier 1014. Charge integrating amplifier 1014 generates an output voltage (e.g., voltage node C) that is the integral of its input voltage (e.g., voltage node B), as shown in FIG. 10B. A/D converter 1018 performs an analog-to-digital conversion of the output of charge integrating amplifier 1014. A/D converter 1018 may be sampled, for example, at some time after time t1 (see FIG. 10B) and its digital V-out value is captured by an external processor (not shown) for analysts. In one example, A/D converter 1018 may be sampled once only at some time after time t1 (see FIG. 10B) to arrive at a measurement of capacitance, C-droplet. In another example, A/D converter 1018 may be sampled multiple times after time t1 and then the multiple digital V-out values may be averaged to arrive at a measurement of capacitance, C-droplet.

In one example application, a capacitance detection circuit of the invention may be used for validating one or more droplet operations on a droplet actuator. For example, the circuit may be used to verify whether one or more droplet operations in a certain protocol have been achieved. In one embodiment, as a certain droplet is moved via droplet operations from one electrode to the next and a capacitance detection operation may occur after each movement to verify that the droplet has moved as expected.

In another example application, a capacitance detection circuit, such as capacitance detection circuit 836, may be used for performing a droplet actuator characterization operation. For example, a droplet may be moved along a line of electrodes toward a designated detection location at a certain droplet actuation frequency. At the end of the sequence, a capacitance detection operation may occur at the designated detection location, to verify that the droplet arrived successfully. This sequence may be repeated at higher and higher droplet actuation frequencies until the droplet actuator fails. In performing this characterization operation using the capacitance detection circuit of the invention, the droplet actuation frequency specification of the droplet actuator may be established.

8.4 Droplet Actuator

For examples of droplet actuator architectures that are suitable for use with the present invention, see U.S. Pat. No. 6,911,132, entitled, "Apparatus for manipulating Droplets by Electrowetting-Based Techniques," issued on Jun. 28, 2005 to Pamula et al.; U.S. patent application Ser. No. 11/343,284, entitled, "Apparatuses and Methods for manipulating Droplets on a Printed Circuit Board," filed on filed on Jan. 30, 2006; U.S. Pat. No. 6,773,566, entitled, "Electrostatic Actuators for microfluidics and Methods for Using Same," issued on Aug. 10, 2004 and U.S. Pat. No. 6,565,727, entitled, "Actuators for Microfluidics Without Moving Parts," issued on Jan. 24, 2000, both to Shenderov et al.; and International Patent Application No. PCT/US 06/47486, entitled, "Droplet-Based Biochemistry," filed by Pollack et al. on Dec. 11, 2006, the disclosures of which are incorporated herein by reference.

8.5 Fluids

For examples of fluids that may be subjected to droplet operations and capacitance detection according to the invention, see the patents listed in section 8.4, especially International Patent Application No. PCT/US 06/47486, entitled, "Droplet-Based Biochemistry," filed on Dec. 11, 2006. In some embodiments, the droplet is a sample fluid, such as a biological sample, such as whole blood, lymphatic fluid, serum, plasma, sweat, tear, saliva, sputum, cerebrospinal fluid, amniotic fluid, seminal fluid, vaginal excretion, serous fluid, synovial fluid, pericardial fluid, peritoneal fluid, pleural fluid, transudates, exudates, cystic fluid, bile, urine, gastric fluid, intestinal fluid, fecal samples, fluidized tissues, fluidized organisms, biological swabs and biological washes. In some embodiment, the fluid that includes a reagent, such as water, deionized water, saline solutions, acidic solutions, basic solutions, detergent solutions and/or buffers. In some embodiments, the fluid includes a reagent, such as a reagent for a biochemical protocol, such as a nucleic acid amplification protocol, an affinity-based assay protocol, a sequencing protocol, and/or a protocol for analyses of biological fluids.

8.6 Filler Fluids

The gap is typically filled with a filler fluid. The filler fluid may, for example, be a low-viscosity oil, such as silicone oil. Other examples of filler fluids are provided in International Patent Application No. PCT/US2006/47486, filed on Dec. 11, 2006, entitled "Droplet-Based Biochemistry".

8.7 Example Method Detecting Capacitance

One approach for providing capacitance detection in a droplet actuator may include, but is not limited to, the steps of providing a mechanism for monitoring the electrode voltage Ve, switching on the electrode voltage Ve and measuring its rise time with no conductive droplet present at a transport electrode of interest, switching off the electrode voltage Ve, providing a conductive droplet at the transport electrode of interest in order to introduce capacitance C-droplet, switching on the electrode voltage Ve and measuring its rise time with conductive droplet present at the transport electrode of interest, calculating the difference between the two rise time measurements, correlating the difference between the two rise time measurements with a capacitance value, and correlating the capacitance value with a droplet footprint area.

Capacitance detection, in general, is particularly suited for most electrowetting applications given the typical physical spacing between electrodes. Moreover, capacitance detection provides a more direct correlation between bead and/or droplet properties than does the measurement of other electrical quantities, such as inductance and impedance. Such other properties typically require additional processing for reactance, time constants and electron propagation factors, among other considerations. In that sense, embodiments determining capacitance require relatively less processing and hardware equipment, while delivering simpler and more accurate calculations than do measurements of other properties. In any case, one skilled in the art will appreciate that preferred embodiments described herein are merely exemplary, and other embodiments consistent with the underlying principles of the present invention may measure capacitance in a number of other manners known its the industry. Furthermore, while various exemplary embodiments are described herein with reference to capacitance, it is understood that other methods can be performed using other types of impedance circuits, such as resistance.

9 CONCLUDING REMARKS

The foregoing detailed description of embodiments refers to the accompanying drawings, which illustrate specific embodiments of the invention. Other embodiments having different structures and operations do not depart from the scope of the present invention.

This specification is divided into sections for the convenience of the reader only. Headings should not be construed as limiting of the scope of the invention.

It will be understood that various details of the present invention may be changed without departing from the scope of the present invention. Furthermore, the foregoing description is for the purpose of illustration only, and not for the purpose of limitation, as the present invention is defined by the claims as set forth hereinafter.

We claim:

1. A method of determining whether a droplet comprises one or more beads, the method comprising:
   (a) providing a droplet on an electrode on a droplet actuator;
   (b) determining capacitance at the electrode;
   (c) comparing the capacitance with an expected capacitance in the presence of one or more beads;
   (d) determining whether one or more beads is present; and wherein the determination:
- (i) follows a droplet splitting operation in a bead washing protocol; and
- (ii) identifies whether bead loss has occurred during the splitting operation.

2. The method of claim 1 wherein the step of providing a droplet on an electrode on a droplet actuator is mediated by a means comprising electrowetting.

3. The method of claim 1 wherein the step of providing a droplet on an electrode on a droplet actuator is not mediated by a means comprising dielectrophoresis.

* * * * *